US009920133B2

(12) United States Patent
Matsumura et al.

(10) Patent No.: US 9,920,133 B2
(45) Date of Patent: Mar. 20, 2018

(54) ANTI-TISSUE FACTOR MONOCLONAL ANTIBODY

(71) Applicants: NATIONAL CANCER CENTER, Tokyo (JP); The University of Tokyo, Tokyo (JP); RIKEN, Wako-shi (JP); NanoCarrier Co., Ltd., Kashiwa-shi (JP)

(72) Inventors: Yasuhiro Matsumura, Kashiwa (JP); Masahiro Yasunaga, Kashiwa (JP); Yoshikatsu Koga, Kashiwa (JP); Yoshiyuki Yamamoto, Kashiwa (JP); Ryuta Sato, Kashiwa (JP); Ryo Tsumura, Kashiwa (JP); Kazunori Kataoka, Tokyo (JP); Nobuhiro Nishiyama, Tokyo (JP); Yutaka Miura, Tokyo (JP); Shino Manabe, Wako (JP); Yasuki Kato, Kashiwa (JP)

(73) Assignees: NATIONAL CANCER CENTER, Tokyo (JP); The University of Tokyo, Tokyo (JP); RIKEN, Wako-shi (JP); NanoCarrier Co., Ltd., Kashiwa-shi (JP)

( * ) Notice: Subject to any disclaimer, the term of this patent is extended or adjusted under 35 U.S.C. 154(b) by 0 days.

(21) Appl. No.: 15/111,875

(22) PCT Filed: Feb. 3, 2015

(86) PCT No.: PCT/JP2015/052918
§ 371 (c)(1),
(2) Date: Jul. 15, 2016

(87) PCT Pub. No.: WO2015/115656
PCT Pub. Date: Aug. 6, 2015

(65) Prior Publication Data
US 2016/0333113 A1    Nov. 17, 2016

(30) Foreign Application Priority Data

Feb. 3, 2014    (JP) .................................. 2014-018586

(51) Int. Cl.
C07K 16/36     (2006.01)
A61K 47/48     (2006.01)
A61K 39/395    (2006.01)
A61K 39/00     (2006.01)

(52) U.S. Cl.
CPC .......... *C07K 16/36* (2013.01); *A61K 39/3955* (2013.01); *A61K 47/48438* (2013.01); *A61K 47/48561* (2013.01); *A61K 2039/505* (2013.01); *C07K 2317/24* (2013.01); *C07K 2317/56* (2013.01); *C07K 2317/565* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,703,494 B2 | 3/2004 | Kirchhofer et al. | |
| 7,435,413 B2 | 10/2008 | Kirchhofer et al. | |
| 7,824,677 B2 | 11/2010 | Wong et al. | |
| 7,968,094 B2 | 6/2011 | Jiao et al. | |
| 8,007,795 B2 | 8/2011 | Jiao et al. | |
| 9,168,314 B2* | 10/2015 | Satijn ............... | A61K 47/48438 |
| 2003/0119075 A1 | 6/2003 | Kirchhofer et al. | |
| 2003/0124117 A1 | 7/2003 | Refino et al. | |
| 2003/0143225 A1 | 7/2003 | Refino et al. | |
| 2004/0126816 A1 | 7/2004 | Kirchhofer et al. | |
| 2012/0039989 A1 | 2/2012 | Hubbell et al. | |
| 2012/0237528 A1 | 9/2012 | Almagro et al. | |
| 2013/0101608 A1 | 4/2013 | Satijn et al. | |

FOREIGN PATENT DOCUMENTS

| | | | | |
|---|---|---|---|---|
| JP | 2003527861 A | | 9/2003 | |
| WO | WO 9405328 A1 * | | 3/1994 | .......... C07K 14/745 |
| WO | 0127160 A1 | | 4/2001 | |
| WO | 01/70984 A2 | | 9/2001 | |
| WO | 03037911 A2 | | 5/2003 | |
| WO | 2004094475 A2 | | 11/2004 | |
| WO | 2011157741 A2 | | 12/2011 | |

OTHER PUBLICATIONS

Chu, A.J., Arch Biochem Biophys. Aug. 15, 2005;440(2):123-32.*
Sato et al., Cancer Research (Apr. 15, 2013) vol. 73, No. 8, Supp. SUPPL.1 Abstract No. 2674.*
Tsumura et al., Cancer Research (Oct. 1, 2014) vol. 74, No. 19 Supp. SUPPL.1 Abstract No. 2062.*
Kipriyanov et al., Mol Biotechnol. Jan. 2004;26(1):39-60.*
Breij, et al., An Antibody-Drug Conjugate That Targets Tissue Factor Exhibits Potent Therapeutic Activity against a Broad Range of Solid Tumors, Cancer Research, Dec. 2013, vol. 74, No. 4, pp. 1214-1226.
English translation of International Search Report dated Apr. 21, 2015 in parent application No. PCT/JP2015/052918.
English translation of the International Preliminary Report on Patentability from the International Preliminary Examination Authority in parent application No. PCT/JP2015/052918.
Partial Supplementary European Search Report from the European Patent Office dated Jul. 14, 2017 in related EP application No. 15 743 456.4, including Search Opinion and Search Report.
Written Opinion of the International Search Authority dated Apr. 21, 2015 in parent PCT application No. PCT/JP2015/052918, including machine translation of rejections provided in Box 2 starting on p. 3 of the Written Opinion.
Communication from European Patent Office dated Oct. 26, 2017 in counterpart EP application No. 15743456.4, Including Search Opinion, Supplementary European Search Report and examined claims 1-6.

* cited by examiner

*Primary Examiner* — Michael Szperka
(74) *Attorney, Agent, or Firm* — J-TEK Law PLLC; Jeffrey D. Tekanic; Scott T. Wakeman

(57) ABSTRACT

Monoclonal antibodies against human and mouse tissue factor, and fragments thereof, are disclosed, as well as pharmaceutical compositions and compositions for drug delivery containing the same. Therapeutic methods using the same are also disclosed.

19 Claims, 8 Drawing Sheets

(a) No.1849

(b) No.1859

(c) No.1006

ANTI-TISSUE FACTOR MONOCLONAL ANTIBODY

CROSS-REFERENCE

This application is the US national stage of International Patent Application No. PCT/JP2015/052918 filed on Feb. 3, 2015, which claims priority to Japanese Patent Application No. 2014-18586 filed on Feb. 3, 2014; all publications, patents, and patent applications cited therein are incorporated herein by reference in their entirety.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
|---|---|---|
| NCC009_sequence.txt | May 24, 2016 | 46 |

TECHNICAL FIELD

The present invention relates to anti-tissue factor monoclonal antibodies and to pharmaceutical compositions utilizing the antibodies.

BACKGROUND ART

In general, when a drug is systemically administered orally or by intravenous injection, the drug is supplied to not only a focus serving as a target of the drug administration but also to normal tissue. As a result, side effects of the drug administration are observed and in some cases the treatment method needs to be changed or stopped. In view of this, for the purpose of reducing side effects, drugs called molecularly targeted drugs have been developed, which have the ability to specifically bind to a molecular marker, such as a receptor, a ligand, or an enzyme, which is unique to the target of the drug administration (for example, Patent Literature 1).

Meanwhile, tissue factor (hereinafter sometimes referred to as "TF") is an initiator of extrinsic coagulation, and its production is promoted by vascular injury or the like. Expression of TF is local and transient in a normal response. However, it is known that, in many solid cancers, such as pancreatic cancer and stomach cancer, the expression of TF is constitutively enhanced at cell surfaces of, for example, cancer cells, vascular endothelial cells, monocytes, and macrophages in tumor tissues.

CITATION LIST

Patent Literature

Patent Literature 1: US 2012/0039989 A1

SUMMARY OF THE INVENTION

An object of the present invention is to provide a novel antibody against TF. In addition, another object of the present invention is to provide a pharmaceutical composition utilizing the antibody as a target-binding factor.

The inventors of the present application have found novel anti-TF monoclonal antibodies having an ability to be internalized by a cell, and further have conceived that a drug can be delivered with high selectivity to a cell expressing TF at its surface by using the antibodies as a target-binding factor, thereby completing the present invention.

That is, according to the present invention, the following monoclonal antibodies, which bind to tissue factor, are provided.

An anti-human tissue factor monoclonal antibody including a heavy chain variable region having complementarity determining regions 1, 2, and 3 containing the amino acid sequences set forth in SEQ ID NOS: 3, 4, and 5, respectively, and a light chain variable region having complementarity determining regions 1, 2, and 3 containing the amino acid sequences set forth in SEQ ID NOS: 6, 7, and 8, respectively;

an anti-human tissue factor monoclonal antibody including a heavy chain variable region having complementarity determining regions 1, 2, and 3 containing the amino acid sequences set forth in SEQ ID NOS: 11, 12, and 13, respectively, and a light chain variable region having complementarity determining regions 1, 2, and 3 containing the amino acid sequences set forth in SEQ ID NOS: 14, 15, and 16, respectively; or an anti-mouse tissue factor monoclonal antibody including a heavy chain variable region having complementarity determining regions 1, 2, and 3 containing the amino acid sequences set forth in SEQ ID NOS: 19, 20, and 21, respectively, and a light chain variable region having complementarity determining regions 1, 2, and 3 containing the amino acid sequences set forth in SEQ ID NOS: 22, 23, and 24, respectively.

According to another aspect of the present invention, monoclonal antibodies are provided, which bind to the same epitope as an epitope of tissue factor to which an above-mentioned monoclonal antibody binds.

According to yet another aspect of the present invention, antibody fragments are provided that include part of an above-mentioned monoclonal antibody, the antibody fragments being capable of binding to tissue factor.

According to yet another aspect of the present invention, pharmaceutical compositions are provided that include: an above-mentioned monoclonal antibody or an above-mentioned antibody fragment as a target-binding factor; and a drug.

According to yet another aspect of the present invention, compositions for drug delivery are provided that include an above-mentioned monoclonal antibody or an above-mentioned antibody fragment as a target-binding factor.

Monoclonal antibodies of the present invention can recognize a cell expressing TF and can have an ability to be internalized by the cell. Accordingly, by using the antibodies as a target-binding factor, a drug can be efficiently delivered to the cell.

DETAILED DESCRIPTION OF THE EMBODIMENTS

[A. Monoclonal Antibody]

Figure 1:
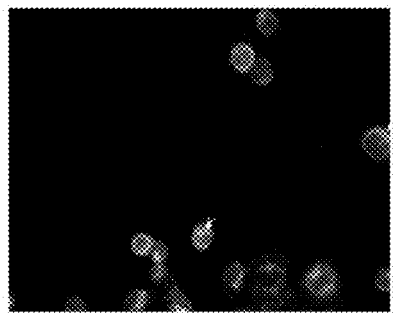
FIGS. 1(a) to 1(c) are micrographs that show the results of an internalization assay.
Figure 1:
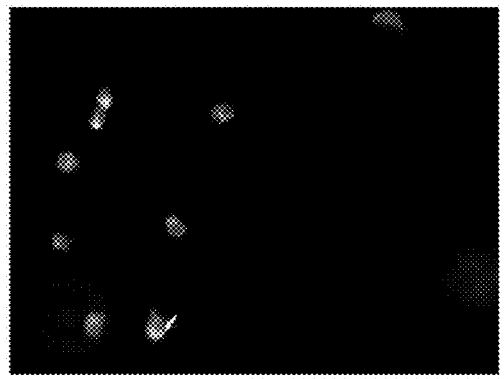
Figure 1:

According to the present invention, monoclonal antibodies that bind to TF are provided. Typically, monoclonal antibodies of the present invention are capable of binding to TF and have an ability to be internalized by a cell expressing TF. TF is blood coagulation factor III, and is expressed at the cell surface as a transmembrane glycoprotein. In the present invention, TF is preferably human TF (hTF). The full-length amino acid sequence of hTF is already known under GenBank ACCESSION_AAA61152 (SEQ ID NO: 1). In the present invention, a monoclonal antibody against mouse TF (mTF) is also provided. The utilization of the anti-mTF monoclonal antibody as a target-binding factor for a drug can be effective in testing or research using mice. The full-length amino acid sequence of mTF is already known under GenBank ACCESSION_AAA63400 (SEQ ID NO: 2).

Herein, internalization means a phenomenon in which an antibody forms an immunocomplex with an antigen at the cell surface and is then taken up into the cell. Whether or not the anti-TF monoclonal antibody has the ability to be internalized may be determined by, for example: a method involving bringing an antibody, which has a labeling substance bound thereto, into contact with a cell expressing TF at its surface, and confirming whether or not the labeling substance has been transferred into the cell; or a method involving bringing an antibody, which has a cytotoxic substance bound thereto, into contact with a cell expressing TF at its surface, and confirming whether or not the contact induces cell death or cell growth inhibition. More specifically, the presence or absence of the ability of an antibody to be internalized may be confirmed by the internalization assay described in Examples.

Any appropriate cell may be used as the cell expressing TF at its surface, and examples thereof include cells in tumor tissues. The expression of TF in a normal tissue is normally a local and transient expression, whereas the expression of TF is constitutively enhanced at cell surfaces of, for example, cancer cells, vascular endothelial cells, monocytes, and macrophages in tumor tissues. Specific examples of the cancer cells include pancreatic cancer cells and stomach cancer cells.

Herein, "monoclonal antibody" refers to antibodies produced by antibody-producing cells that are monoclonal. Monoclonal antibodies have uniform primary structures and recognize the same epitope. Monoclonal antibodies of the present invention have a basic structure formed of a tetramer in which two identical heavy chains and two identical light chains are bound by disulfide bonds. Anti-TF monoclonal antibodies of the present invention may be any isotype of IgG, IgA, IgM, IgD, or IgE. Of those, IgG is preferred.

An epitope that anti-TF monoclonal antibodies of the present invention recognizes is preferably present in the extracellular domain of TF.

The dissociation constant (KD) of anti-TF monoclonal antibodies of the present invention for TF reaches, for example, $5\times10^{-9}$ M or less, even $1\times10^{-9}$ M or less, particularly $2\times10^{-10}$ M or less. The dissociation constant may be measured, for example, using a surface plasmon resonance method.

Anti-IF monoclonal antibodies of the present invention may or may not exhibit anticoagulant activity. The presence or absence of anticoagulant activity or its degree may be determined based on prothrombin time (PT). An anti-TF monoclonal antibody exhibiting no anticoagulant activity or low anticoagulant activity is hardly captured by a blood clot or the like, and hence its utilization as a target-binding factor for a drug can improve the deliverability of the drug to a target site, with the result that the efficacy of the drug can be suitably exhibited. The prolonged coagulation time ratio (ratio relative to PBS) of anti-TF monoclonal antibodies of the present invention, in the state that an antigen-antibody complex has been formed, is preferably 3 or less, more preferably 2 or less, still more preferably from 1 to 1.5. The prolonged coagulation time ratio, in the state that an antigen-antibody complex has been formed, may be determined by the method described in Examples.

[A-1. Anti-hTF Monoclonal Antibodies]

In a first embodiment, an anti-hTF monoclonal antibody of the present invention includes a heavy chain variable region having complementarity determining regions (CDR) 1, 2, and 3 containing the amino acid sequences set forth in SEQ ID NOS: 3, 4, and 5, respectively, and a light chain variable region having CDR1, CDR2, and CDR3 containing the amino acid sequences set forth in SEQ ID NOS: 6, 7, and 8, respectively. A preferred specific example thereof may be an anti-hTF monoclonal antibody including a heavy chain variable region containing the amino acid sequence set forth in SEQ ID NO: 9, and a light chain variable region containing the amino acid sequence set forth in SEQ ID NO: 10.

In a second embodiment, an anti-hTF monoclonal antibody of the present invention includes a heavy chain variable region having CDR1, CDR2, and CDR3 containing the amino acid sequences set forth in SEQ ID NOS: 11, 12, and 13, respectively, and a light chain variable region having CDR1, CDR2, and CDR3 containing the amino acid sequences set forth in SEQ ID NOS: 14, 15, and 16, respectively. A preferred specific example thereof may be an anti-hTF monoclonal antibody including a heavy chain variable region containing the amino acid sequence set forth in SEQ ID NO: 17, and a light chain variable region containing the amino acid sequence set forth in SEQ ID NO: 18.

Variants of each monoclonal antibody exemplified in the first or second embodiment may also be encompassed in anti-hTF monoclonal antibodies of the present invention. Examples of the variants are monoclonal antibodies, in which the heavy chain variable region and/or the light chain variable region contain(s) one or several (for example, one to ten, preferably one to five) amino acid substitutions, insertions, additions, and/or deletions. Such variants can also suitably bind to hTF and have the ability to be internalized by a cell expressing hTF.

Specific examples of variants of the monoclonal antibodies are monoclonal antibodies including a heavy chain variable region containing an amino acid sequence which is preferably 90% or more, more preferably 95% or more, still more preferably 98% or more identical to the amino acid sequence set forth in SEQ ID NO: 9, and a light chain variable region containing an amino acid sequence which is preferably 90% or more, more preferably 95% or more, still more preferably 98% or more identical to the amino acid sequence set forth in SEQ ID NO: 10. In addition, other specific examples of the variants are monoclonal antibodies including a heavy chain variable region containing an amino acid sequence which is preferably 90% or more, more preferably 95% or more, still more preferably 98% or more identical to the amino acid sequence set forth in SEQ ID NO: 17, and a light chain variable region containing an amino acid sequence which is preferably 90% or more, more preferably 95% or more, still more preferably 98% or more identical to the amino acid sequence set forth in SEQ ID NO: 18. It is preferred that any such variant be capable of binding to hTF and have the ability to be internalized by a cell expressing hTF.

Variants of the monoclonal antibodies may contain, in at least one of the CDRs of the heavy chain variable region and/or the light chain variable region of its corresponding monoclonal antibody, one or several, for example, one, two, or three, preferably one or two, more preferably one amino acid substitution, insertion, addition, and/or deletion. Each CDR of the variant has a homology of preferably from 90% to 100% to each CDR of its corresponding monoclonal antibody, and the homology is more preferably from 95% to 100%, still more preferably from 98% to 100%, most preferably 100%. In addition, the entire CDR1 to CDR3 of the heavy chain and the light chain of the variants have a homology of preferably from 90% to 100% to the entire CDR1 to CDR3 of the heavy chain and the light chain of its corresponding monoclonal antibody, and the homology is more preferably from 95% to 100%, still more preferably from 98% to 100%, most preferably 100%.

In a third embodiment, anti-hTF monoclonal antibodies of the present invention may be monoclonal antibodies that bind to the same epitope as an epitope of hTF to which the monoclonal antibodies exemplified in the first or second embodiment binds. Antibodies that bind to the same epitope may be obtained by a known method such as a competitive ELISA method. In a competitive ELISA method, for example, if the antibody serving as the test subject decreases the binding activity of a control antibody (that is, the monoclonal antibody exemplified in the first or second embodiment) by 30% or more, preferably 40% or more, more preferably 50% or more, as compared to the binding activity of the control antibody in the absence of the antibody serving as the test subject, the antibody serving as the test subject may be said to be an antibody that binds to substantially the same epitope as the control antibody. It is preferred that the antibody that binds to the same epitope be capable of binding to hTF and have the ability to be internalized by a cell expressing hTF. It should be noted that, in such embodiments, the antibody that binds to the same epitope may be a variant of the monoclonal antibodies exemplified in the first or second embodiment.

Anti-hTF monoclonal antibodies of the present invention described above may be a human chimeric antibody or a humanized antibody.

"Human chimeric antibody" refers to an antibody in which a variable region of an antibody of non-human mammalian origin and a constant region of an antibody of human origin are linked to each other. Accordingly, human chimeric antibodies of the present invention may be a chimeric antibody obtained by linking the heavy chain variable region and the light chain variable region of a monoclonal antibody exemplified in the first, second, or third embodiment to a human heavy chain constant region and a human light chain constant region, respectively.

Specifically, an example of a human chimeric antibody of the present invention is a chimeric antibody in which a heavy chain variable region containing the amino acid sequences set forth in SEQ ID NOS: 3, 4, and 5 as heavy chain CDR1, CDR2, and CDR3, respectively, and a light chain variable region containing the amino acid sequences set forth in SEQ ID NOS: 6, 7 and 8 as light chain CDR1, CDR2, and CDR3, respectively are linked to a human heavy chain constant region and a human light chain constant region, respectively. A specific example of such a chimeric antibody is a chimeric antibody in which a heavy chain variable region containing the amino acid sequence set forth in SEQ ID NO: 9 and a light chain variable region containing the amino acid sequence set forth in SEQ ID NO: 10 are linked to a human heavy chain constant region and a human light chain constant region, respectively.

Another example of the human chimeric antibody of the present invention is a chimeric antibody in which a heavy chain variable region containing the amino acid sequences set forth in SEQ ID NOS: 11, 12, and 13 as heavy chain CDR1, CDR2, and CDR3, respectively, and a light chain variable region containing the amino acid sequences set forth in SEQ ID NOS: 14, 15, and 16 as light chain CDR1, CDR2, and CDR3, respectively are linked to a human heavy chain constant region and a human light chain constant region, respectively. A specific example of such a chimeric antibody is a chimeric antibody in which a heavy chain variable region containing the amino acid sequence set forth in SEQ ID NO: 17 and alight chain variable region containing the amino acid sequence set forth in SEQ ID NO: 18 are linked to a human heavy chain constant region and a human light chain constant region, respectively.

The heavy chain constant region of the human chimeric antibody only needs to be one belonging to a human immunoglobulin (hereinafter described as hIg), and preferably belongs to the hIgG class. Similarly, the light chain constant region of the human chimeric antibody only needs to be one belonging to hIg, and may be belong to either one of the κ class and the λ class.

"Humanized antibody" refers to an antibody in which CDRs of an antibody of non-human mammalian origin are grafted at the appropriate location in a variable region of an antibody of human origin. Accordingly, humanized antibody of the present invention may be a human antibody which has the CDR1 to CDR3 of the heavy chain and the light chain of a monoclonal antibody exemplified in the first, second, or third embodiment, as the CDR1 to CDR3 of the heavy chain and the light chain, and in which the other regions are derived from a human antibody.

Specific examples of humanized antibodies of the present invention include: a humanized antibody in which CDR1, CDR2, and CDR3 of the heavy chain have the amino acid sequences set forth in SEQ ID NOS: 3, 4, and 5, respectively, CDR1, CDR2, and CDR3 of the light chain have the amino acid sequences set forth in SEQ ID NOS: 6, 7, and 8, respectively, and the other regions are derived from a human antibody; and a humanized antibody in which CDR1, CDR2, and CDR3 of the heavy chain have the amino acid sequences set forth in SEQ ID NOS: 11, 12, and 13, respectively, CDR1, CDR2, and CDR3 of the light chain have the amino acid sequences set forth in SEQ ID NOS: 14, 15, and 16, respectively, and the other regions are derived from a human antibody.

The heavy chain of the humanized antibody only needs to be one belonging to hIg, and preferably belongs to the hIgG class. Similarly, the light chain of the humanized antibody only needs to be one belonging to hIg, and may belong to either one of the κ class and the λ class.

[A-2. Anti-mTF Monoclonal Antibodies]

In one embodiment, an anti-mTF monoclonal antibody of the present invention includes a heavy chain variable region having CDR1, CDR2, and CDR3 containing the amino acid sequences set forth in SEQ ID NOS: 19, 20, and 21, respectively, and a light chain variable region having CDR1, CDR2, and CDR3 containing the amino acid sequences set forth in SEQ ID NOS: 22, 23, and 24, respectively. A preferred specific example thereof may be an anti-mTF monoclonal antibody including a heavy chain variable region containing the amino acid sequence set forth in SEQ ID NO: 25, and a light chain variable region containing the amino acid sequence set forth in SEQ ID NO: 26.

Variants of the monoclonal antibodies exemplified above may also be encompassed in anti-mTF monoclonal antibodies of the present invention. Examples of variants are monoclonal antibodies in which the heavy chain variable region and/or the light chain variable region contain(s) one or several (for example, one to ten, preferably one to five) amino acid substitutions, insertions, additions, and/or deletions. Such variants can also suitably bind to mTF and have the ability to be internalized by a cell expressing mTF.

Specific examples of variants of the monoclonal antibodies are monoclonal antibodies including a heavy chain variable region containing an amino acid sequence which is preferably 90% or more, more preferably 95% or more, still more preferably 98% or more identical to the amino acid sequence set forth in SEQ ID NO: 25, and a light chain variable region containing an amino acid sequence which is preferably 90% or more, more preferably 95% or more, still more preferably 98% or more identical to the amino acid sequence set forth in SEQ ID NO: 26. It is preferred that such variants be capable of binding to mTF and have the ability to be internalized by a cell expressing mTF.

Variants of the monoclonal antibodies may contain, in at least one of the CDRs of the heavy chain variable region and/or the light chain variable region of its corresponding monoclonal antibody, one or several, for example, one, two, or three, preferably one or two, more preferably one amino acid substitution, insertion, addition, and/or deletion. Each CDR of the variants has a homology of preferably from 90% to 100% to each CDR of its corresponding monoclonal antibody, and the homology is more preferably from 95% to 100%, still more preferably from 98% to 100%, most preferably 100%. In addition, the entire CDR1 to CDR3 of the heavy chain and the light chain of the variant have a homology of preferably from 90% to 100% to the entire CDR1 to CDR3 of the heavy chain and the light chain of its corresponding monoclonal antibody, and the homology is more preferably from 95% to 100%, still more preferably from 98% to 100%, most preferably 100%.

In another embodiment, anti-mTF monoclonal antibodies of the present invention may be monoclonal antibodies that bind to the same epitope as the epitope of mTF to which the monoclonal antibody exemplified above binds. It is preferred that antibodies that binds to the same epitope be capable of binding to mTF and have the ability to be internalized by a cell expressing mTF. In such embodiments, the antibodies that bind to the same epitope may be variants of the monoclonal antibody exemplified above. It should be noted that a method of obtaining antibodies that bind to the same epitope is described above.

[B. Production Method for Monoclonal Antibodies]

B-1. Production of Monoclonal Antibodies Using Hybridomas

Monoclonal antibodies of the present invention may be obtained by, for example, preparing hybridomas through cell fusion between antibody-producing cells obtained from an animal immunized with an antigen and myeloma cells, selecting, from the resultant hybridomas, hybridomas which produce an antibody of interest, and allowing the selected hybridomas to produce the antibody.

B-1-1. Preparation of Antigen

As the antigen to be used in the immunization of the animal, for example, TF (full-length TF) or a partial peptide thereof, or a cell expressing TF at its surface may be used. hTF may be obtained by, for example, purifying hTF derived from a human placenta according to the method disclosed in JP 09-302000 A or the like. In addition, for example, TF or a partial peptide thereof may be obtained by a genetic engineering method or a chemical synthesis method. A partial peptide may be used by being bound to any appropriate carrier protein as necessary. It should be noted that the mRNA sequence of hTF is known under GenBank NM_001993.4 (SEQ ID NO: 27). In addition, the mRNA sequence of mTF is known under GenBank M57896.1 (SEQ ID NO: 28).

B-1-2. Preparation of Antibody-Producing Cells

The antigen obtained as described above is mixed with any appropriate adjuvant, and is administered to a non-human mammal, such as a mouse, a rat, a horse, a monkey, a rabbit, a goat, or a sheep, to immunize the non-human mammal. The antibody titer of the immunized animal against the antigen is measured, and an animal having a high antibody titer is subjected to final immunization. Several days after the day of the final immunization, antibody-producing cells, such as spleen cells or lymph node cells, are collected. Details of a method for the immunization and a method of collecting the antibody-producing cells are well known to persons skilled in the art, and hence a detailed description thereof is omitted. The antibody titer may be measured by, for example, an enzyme immunoassay (EIA), such as an ELISA method, or a radioimmunoassay (RIA), with blood collected from the animal.

B-1-3. Cell Fusion

As the myeloma cells to be fused with the antibody-producing cells, any appropriate cell line which is derived from an animal, such as a mouse or a rat, and which is generally available to persons skilled in the art may be used. It is preferred to use myeloma cells having drug resistance and having the following properties: being unable to survive in a selection medium (such as a medium containing hypoxanthine, aminopterin, and thymidine (HAT medium)) in an unfused state and being able to survive therein only in a fused state. The cell fusion may be performed using any appropriate method, such as a PEG method or an electro-fusion method. Then, after the cell fusion treatment the cells are suspended and diluted in a selection medium (such as HAT medium), and cultured in wells of a culture plate.

B-1-4. Screening and Cloning of Hybridomas

Cells which have formed colonies as a result of culturing after the cell fusion are selected as hybridomas. Then, the selected hybridomas are, for example, cultured in a microtiter plate, and the resultant culture supernatant is collected and measured for reactivity to the antigen. The reactivity to the antigen may be measured by EIA, RIA, or the like. Hybridomas showing reactivity to the antigen as a result of the measurement are selected, and monoclonal antibody-producing hybridomas are isolated by a limiting dilution method or the like.

B-1-5. Preparation of Monoclonal Antibodies from Hybridomas

Monoclonal antibodies may be prepared by, for example: a method involving culturing the hybridomas in any appropriate medium, and purifying the monoclonal antibody from the resultant culture supernatant; or a method involving injecting the hybridomas into the abdominal cavity of a non-human mammal, such as a mouse or a rat, to culture the hybridomas in peritoneal fluid, and purifying the monoclonal antibody from the resultant peritoneal fluid. The antibodies may be purified by using, for example, an ammonium sulfate precipitation method, a gel-filtration chromatography method, an ion-exchange chromatography method, and an affinity column chromatography method, such as an anti-immunoglobulin column or a protein A column in combination as necessary.

B-2. Production of Monoclonal Antibodies Using Genetic Engineering Techniques

Monoclonal antibodies of the present invention may be produced by, for example, genetic engineering techniques through the utilization of an antibody gene cloned from antibody-producing cells, such as the hybridomas.

B-2-1. Cloning of Gene Encoding Variable Region

Total mRNA is extracted from hybridomas that produce the antibody of interest, and cDNA encoding an antibody variable region is synthesized from the resultant total mRNA with reverse transcriptase by using sequences common to antibody genes as primers. The synthesis and amplification of the cDNA may be performed using, for example, a 5'-RACE method, and at that time, any appropriate restriction enzyme site may be introduced at both ends of the cDNA. A DNA fragment of interest is purified from the resultant PCR product, linked to vector DNA, and introduced into *Escherichia coli* or the like, to thereby prepare a desired recombinant vector. Then, the base sequence of the antibody gene of interest is confirmed by a known method, such as a deoxy method.

B-2-2. Introduction of Antibody Gene into Host Cell

The DNA encoding the variable region cloned as described above is linked to DNA encoding a desired antibody constant region, and the resultant is incorporated into an expression vector. As an alternative, the DNA encoding the variable region may be incorporated into an expression vector containing DNA encoding the desired constant region. The thus-obtained expression vector may be introduced into any appropriate host cell, to thereby express the antibody. In this case, the heavy chain and the light chain may be separately incorporated into expression vectors, followed by simultaneous introduction of these two expression vectors into the same host cell, or DNA encoding the heavy chain or the light chain may be incorporated into a single expression vector to be introduced into a host cell. It should be noted that the DNA encoding the variable region may also be obtained by performing a total synthesis based on the base sequence determined in section B-2-1 by using an artificial gene synthesis service or the like. Examples of the host cell include animal cells, plant cells, insect cells, yeasts, and bacteria.

B-2-3. Preparation of Monoclonal Antibodies from Host Cell

Monoclonal antibodies may be obtained by culturing the host cell, which has the expression vector incorporated therein, in any appropriate medium, and purifying the monoclonal antibodies from the resultant culture supernatant. A method of purifying antibodies is described above.

B-3. Production of Chimeric Antibodies

Human chimeric antibodies may be obtained by, for example, linking DNA encoding a variable region of a monoclonal antibody obtained in the same manner as above to DNA encoding a constant region of a human antibody, incorporating the resultant into an expression vector, and introducing the expression vector into a host to express human chimeric antibodies (for example, WO 95/14041 A1).

B-4. Production of Humanized Antibodies

Humanized antibodies may be obtained by grafting CDRs of an antibody of a non-human mammal into a human antibody so that the CDRs are linked to the framework region of the human antibody through the use of so-called CDR grafting techniques. A method of grafting CDRs of an antibody of a non-human mammal (such as a mouse) into a human framework region is known, and an example thereof is an overlap extension PCR method.

In general, in CDR grafting, it is advantageous in maintaining the function of the CDRs to select a human framework region having a high homology to the framework region of the antibody of the non-human mammal. Accordingly, it is preferred to utilize a human framework region having an amino acid sequence having a high homology to the amino acid sequence of the framework region adjacent to the CDRs to be grafted.

[C. Antibody Fragments]

The present invention also provides antibody fragments that include part of a monoclonal antibody described in section A, the antibody fragments being capable of binding to tissue factor. Antibody fragments of the present invention typically have the ability to be internalized by a cell expressing tissue factor. Examples of the antibody fragments include Fab, F(ab')$_2$, Fab', a single-chain antibody (scFv), a disulfide-stabilized antibody (dsFv), a dimerized V region fragment (diabody), and a CDR-containing peptide.

The Fab may be obtained by subjecting the monoclonal antibody to papain treatment. In addition, the Fab may also be obtained by inserting DNA encoding the Fab of the monoclonal antibody into any appropriate expression vector, and introducing the vector into a host cell to express the Fab.

The F(ab')$_2$ may be obtained by subjecting the monoclonal antibody to pepsin treatment. In addition, the F(ab')$_2$ may also be obtained by inserting DNA encoding the F(ab')$_2$ of the monoclonal antibody into any appropriate expression vector, and introducing the vector into a host cell to express the F(ab')$_2$.

The Fab' is an antibody fragment obtained by cleaving the S—S bond between the hinges of F(ab')$_2$. The Fab' may be obtained by subjecting the F(ab')$_2$ to treatment with the reducing agent dithiothreitol. In addition, the Fab' may also be obtained by inserting DNA encoding the Fab' into any appropriate expression vector, and introducing the vector into a host cell to express the Fab'.

The scFv is such that only the variable regions of a heavy chain and a light chain are linked via an appropriate peptide linker. The scFv may be obtained by constructing an expression vector for the scFv based on the DNA encoding the heavy chain variable region and the light chain variable region of the monoclonal antibody, and introducing the vector into a host cell to express the scFv.

The dsFv is such that polypeptides obtained by substituting one amino acid residue in each of a heavy chain variable region and a light chain variable region with a cysteine residue are bound via a S—S bond. The location at which the cysteine residue is introduced in each region may be determined based on a three-dimensional structure predicted by molecular modeling. The dsFv may be obtained by constructing an expression vector for the dsFv based on the DNA encoding the heavy chain variable region and the light chain variable region of the monoclonal antibody, and introducing the vector into a host cell to express the dsFv.

The diabody is a dimer of scFvs linked via a short peptide linker having eight or less amino acid residues, and has divalent antigen binding activity. The divalent antigen binding activity may be identical or different from each other. The diabody may be obtained by constructing an expression vector for scFvs linked via a peptide linker having eight or less amino acid residues based on the DNA encoding the heavy chain variable region and the light chain variable region of the monoclonal antibody, and introducing the vector into a host cell to express the diabody.

The CDR-containing peptide contains at least one of the CDRs of a heavy chain variable region or a light chain variable region. The CDR-containing peptide may be such that a plurality of CDRs are bound directly or via an appropriate peptide linker. The CDR-containing peptide may be obtained by inserting DNA encoding the CDRs in the heavy chain variable region and the light chain variable region of the monoclonal antibody into any appropriate expression vector, and introducing the vector into a host cell to express the CDR-containing peptide. In addition, the CDR-containing peptide may also be obtained by a chemical synthesis method, such as an Fmoc method or a tBoc method.

[D. Pharmaceutical Composition]

Pharmaceutical compositions of the present invention include: a monoclonal antibody described in section A or an antibody fragment described in section C as a target-binding factor; and a drug. Utilization of a monoclonal antibody or an antibody fragment (hereinafter sometimes referred to as "monoclonal antibody or the like") as the target-binding factor allows a drug to be efficiently delivered into a cell expressing TF at its surface.

In a first embodiment, the monoclonal antibody or the like may be in a state of being bound to the drug. In addition, in such embodiment, as necessary, a polymer compound may be further bound to the monoclonal antibody or the like.

Any appropriate drug may be selected as the drug depending on the disease to be treated and the like. Examples thereof include: biologics, such as nucleic acid pharmaceuticals, antibody pharmaceuticals, and gene therapy drugs; and cytotoxic molecules, such as cytotoxins and cytotoxic drugs.

Examples of the nucleic acid pharmaceuticals include plasmid DNA, siRNA, micro RNA, shRNA, an antisense nucleic acid, a decoy nucleic acid, an aptamer, and a ribozyme site.

Examples of the cytotoxins include taxol, cytochalasin B, gramicidin D, ethidium bromide, emetine, mitomycin, etoposide, teniposide, vincristine, vinblastine, colchicine, doxorubicin, daunorubicin, dihydroxyanthracenedione, mitoxantrone, mithramycin, actinomycin D, 1-dehydrotestosterone, glucocorticoid, procaine, tetracaine, lidocaine, propranolol, puromycin, duocarmycin, calicheamicin, maytansine, auristatin, and derivatives thereof.

Examples of the cytotoxic drugs include: metabolic antagonists, suchasmethotrexate, 6-mercaptopurine, 6-thioguanine, cytarabine, 5-fluorouracil, and decarbazine; alkylating agents, such as mechlorethamine, Thio-TEPA, chlorambucil, melphalan, carmustine (BSNU), lomustine (CCNU), cyclophosphamide, busulfan, dibromomannitol, streptozocin, mitomycin C, and cis-dichlorodiaminoplatinum(II); antibiotics, such as anthracyclines including daunorubicin and doxorubicin, dactinomycin, bleomycin, mithramycin, and anthramycin (AMC); and antimitotic agents, such as vincristine and vinblastine.

The binding between the drug or the polymer compound and the monoclonal antibody or the like may be performed by a method known in the art. The binding may be performed by, for example, allowing respective functional groups thereof or functional groups introduced as necessary to react with each other. As a combination of the functional groups, there are given, for example, an amino group and a carboxyl group, a carboxyl group and a hydroxyl group, a maleimide group and a thiol group, a thiol group and a thiol group, a hydrazide group and a ketone group, a hydrazide group and an aldehyde group, an amino group and an aldehyde group, a thiol group and a carboxyl group, an amino group and a squaric acid derivative, a dienyl aldehyde group and an amino group, a halo ester and a thiol group, and an azide and an alkyne. In addition, for example, when the drug is a protein or a peptide, the pharmaceutical composition may contain a fusion protein of the drug and the monoclonal antibody or the like which can be obtained by genetic engineering techniques. Further, when the drug has a charge, the drug may also be bound via an ionic bond.

Any appropriate polymer compound may be selected as the polymer compound. Specific examples thereof include polyethylene glycol, albumin, dextran, polyvinylpyrrolidone, and polyvinyl alcohol. When any such polymer compound is bound, stability in blood can be improved.

The binding site of the polymer compound may be any appropriate site as long as the antigen binding activity and ability to be internalized of the monoclonal antibody or the like are not impaired.

In a second embodiment, the monoclonal antibody or the like may be in a state of being bound to a DDS carrier material. As the DDS carrier material, one capable of forming drug-encapsulated nanoparticles (for example, particles having an average particle diameter of preferably from 10 nm to 400 nm, more preferably from 20 nm to 300 nm, still more preferably from 30 nm to 150 nm) may be preferably used. With the use of such a DDS carrier material, drug-encapsulated nanoparticles can be formed, and hence the in vivo stability of the drug can be improved, and besides, sustained release thereof can be achieved. Further, reliable drug delivery into a target cell by the monoclonal antibody or the like can be achieved.

The monoclonal antibody or the like may be bound at any appropriate location in the DDS carrier material. From the viewpoint of enabling target binding properties to be suitably exhibited, it is preferred that the monoclonal antibody or the like be bound so as to be exposed at the outer surfaces of the nanoparticles formed by the DDS carrier material. The binding between the monoclonal antibody or the like and the DDS carrier material may be performed by, for example, allowing respective functional groups thereof or functional groups introduced as necessary to react with each other. A preferred combination of the functional groups is as described above.

Examples of the DDS carrier material include: polymer micelle-forming materials, such as a block copolymer having a hydrophilic segment and a hydrophobic segment; liposome-forming materials, such as a phospholipid; nanohydrogel capsule-forming materials, such as natural polymers, such as gelatin, collagen, hyaluronic acid, and alginic acid, and synthetic polymers, such as polyethylene glycol and polyvinyl alcohol; and nanosphere-forming materials, such as polyglycolic acid, polylactic acid, and copolymers thereof. Of those, a block copolymer having a hydrophilic segment and a hydrophobic segment is preferably used.

When the monoclonal antibody or the like is bound to the hydrophilic segment of the block copolymer having a hydrophilic segment and a hydrophobic segment to prepare a block copolymer having a target binding property, a polymer micelle capable of delivering the drug to a target cell with high reliability can be obtained.

As the drug, a drug similar to that in the first embodiment may be used. In the second embodiment, the drug may be used as is, or may be used in the form of a drug-bound block copolymer by being bound to the hydrophobic segment of the block copolymer having a hydrophilic segment and a hydrophobic segment.

[E. Compositions for Drug Delivery]

Compositions for drug delivery of the present invention include a monoclonal antibody described in section A or an antibody fragment described in section C. The monoclonal antibody or the antibody fragment can be utilized as a target-binding factor for a cell expressing TF, and can exhibit the ability to be internalized by the cell. Accordingly, when a drug is administered using a composition for drug delivery of the present invention, the drug can be efficiently delivered into a cell expressing TF at its surface.

[F. Applications of Anti-TF Monoclonal Antibodies of the Present Invention]

Anti-TF monoclonal antibodies of the present invention are typically used for treatment of a disease associated with tissue factor (such as a disease involving enhanced expression of tissue factor at a tissue or cell surface). Examples of diseases associated with tissue factor include cancer, inflammation, and thrombosis. The expression of TF is constitutively enhanced in various cancer tissues, and hence anti-TF monoclonal antibodies can be used for treatment of cancer irrespective of its kind. In addition, for example with respect to pancreatic cancer, the prognosis of patients who highly express TF has been reported to be poor, and it may be effectively utilized also in treatments targeting such patients.

The administration route of the pharmaceutical composition of the present invention is preferably parenteral administration, such as subcutaneous, intravenous, intra-arterial, or local administration, particularly preferably intravenous injection. The dose may be appropriately determined depending on, for example, the kind of the drug, the dosage regimen, the age and gender of the patient, and the patient's state of health.

EXAMPLES

In the following, the present invention is described in more detail by way of Examples. However, the present invention is by no means limited to these Examples. It should be noted that the term "part(s)" and the term "%" mean "part(s) by weight" and "wt %", respectively.

Example 1: Anti-hTF Monoclonal Antibodies and Fragments Thereof

[Preparation of Antigen]

A recombinant protein containing an amino acid sequence from position 33 to position 251 in the full-length amino acid sequence of hTF was expressed using *Escherichia coli*, and purified with a nickel column to afford recombinant hTF (SEQ ID NO: 29), which was used as the antigen.

[Immunization of Rats]

50 μg of the recombinant hTF was intraperitoneally coadministered with Freund's complete adjuvant (Difco) to three 6-week-old Wistar female rats and thus the initial immunization was performed. After 14 days therefrom, 50 μg of the recombinant hTF was coadministered with Sigma Adjuvant System® (Sigma) and thus a booster immunization was performed. Thereafter, similar booster immunizations were performed every 21 days five times. After an additional 126 days, 10 μg of the recombinant hTF diluted with PBS was intraperitoneally administered and 40 μg of the recombinant hTF was administered to the tail vein; thus, the final immunization was performed.

[Preparation of Hybridomas]

After 3 days from the final immunization, the spleen was excised, and spleen cells were collected. The spleen cells and mouse myeloma cells (p3X63Ag8.653) were fused using polyethylene glycol 4000 (Merck) at a concentration of 50%, and selection was performed with HAT medium.

[Screening of Antibody-Producing Hybridomas]

After 8 days from the cell fusion, screening of antibody-producing hybridomas was performed. The immunoassay used for the screening is the following. For an ELISA method, a 50 mM carbonate buffer (pH 8) containing 1 μg/mL of the recombinant hTF was added to each well of a 96-well microtiter plate (manufactured by Nunc) at 50 μL/well, and immobilization was performed at 4° C. overnight or at room temperature for 2 hours. The wells were washed three times with 300 μL of a washing solution (0.05% Tween 20/25 mM Tris/140 mM NaCl/2.5 mM KCl, pH 7.4), and then 200 μL of a blocking buffer (0.05% Tween 20/1% BSA/100 mM $NaH_2PO_4$/140 mM NaCl, pH 5) was added, followed by standing at 4° C. overnight or at room temperature for 1 hour to undergo blocking. 50 μL of a hybridoma culture supernatant was added to each well of the thus-obtained hTF-immobilized plate and the mixture was allowed to react at room temperature for 1 hour. Each well was washed three times with 300 μL of the washing solution. After that, 50 μL of an HRP-labeled anti-mouse IgG antibody (Bethyl) diluted 5,000-fold with the blocking buffer was added, and the mixture was allowed to react for 30 minutes. After the reaction, each well was washed three times with 300 μL of the washing solution, and 100 μL of 3.7 mM o-phenylenediamine/25 mM citric acid/130 mM $Na_2HPO_4$/0.006% $H_2O_2$ (pH 5.0) was added to develop color. After from 10 minutes to 15 minutes, 2 N sulfuric acid was added at 30 μL/well to stop the reaction, and absorbance (490 nM) was measured with an absorbance plate reader. In addition, an immunoprecipitation ELISA method was performed by mixing the recombinant hTF and the hybridoma culture supernatant, and measuring the amount of unbound hTF in the mixed liquid using an hTF-quantifying sandwich ELISA. Further, a flow cytometry method was performed in accordance with a conventional method to measure the reactivity of the hybridoma culture supernatant to hTF-expressing cells.

Hybridomas that showed a strong affinity for hTF as a result of the measurement were selected, and a limiting dilution method was performed twice for clones of the hybridomas to establish hybridoma clones producing monoclonal antibodies that bind to hTF.

[Preparation of Antibodies]

Each established hybridoma was mass-cultured in, for example, RPMI 1640 medium containing bovine serum in an amount of 5% having removed therefrom IgG of bovine origin, to afford a culture supernatant. Alternatively, each hybridoma was mass-cultured in the abdominal cavity of ICR nude mice, and peritoneal fluid was collected. The resultant culture supernatant or peritoneal fluid was subjected to Protein G affinity column chromatography to purify IgG monoclonal antibodies.

[Internalization Assay]

Each monoclonal antibody obtained as described above was subjected to the following internalization assay.

Pancreatic cancer cells BxPC3 that express TF in high amounts were seeded into a four-chamber Culture Slide (BD) at $5 \times 10^4$ cells/chamber, and cultured in RPMI 1640 medium at 37° C. under a 5% $CO_2$ environment for 12 hours. The resultant was washed three times with PBS, and then 30 µg of antibody labeled with an Alexa 647 fluorescence labeling kit (Invitrogen) was diluted with 1 ml of RPMI 1640 medium and added to each chamber, followed by culturing for 3 hours. After 2 hours from the initiation of this culturing, Lysotracker® RED-DND99 (Invitrogen) was added to the culture solution to have a final concentration of 75 nM, followed by further culturing for 1 hour. Then, the resultant was washed three times with PBS. After that, immobilization was performed with 4% paraformaldehyde, and nuclear staining was performed with 4',6-diamidino-2-phenylindole (DAPI), followed by mounting with Fluoromount-G® (Southern Biotech). Then, the cells were observed using a fluorescence microscope (Keyence). The results of the observation are shown in FIG. 1.

As shown in FIG. 1(a) and FIG. 1(b), in two of the monoclonal antibodies (No. 1849 and No. 1859), the labeling substance transferred into cells, and thus it was confirmed that these monoclonal antibodies had the ability to be internalized. On the other hand, the ability to be internalized was not confirmed for the antibody shown in FIG. 1(c). It should be noted that the subclasses of those antibodies were determined using Mouse Monoclonal Antibody Isotyping ELISA Kit (manufactured by BD Biosciences) and the results were as follows: the subclass of No. 1849 was IgG2b and the subclass of No. 1859 was IgG2a.

[Determination of DNA Sequences Encoding Variable Regions, Amino Acid Sequences, and CDR Sequences]

1. Anti-hTF Monoclonal Antibody (No. 1849)

Total RNA was extracted from hybridomas producing the anti-hTF monoclonal antibody (No. 1849), and then cDNA was synthesized from the resultant total RNA, in accordance with a conventional method.

DNA fragments encoding the heavy chain variable region and the light chain variable region of the anti-hTF monoclonal antibody (No. 1849) were obtained by a PCR method using the synthesized cDNA as a template. Specifically, PCR was performed using, from the following list of primers, a mixed primer of the following primers 1 to 19 and the following primer 20 as a sense primer and antisense primer for heavy chain variable region cloning, respectively, and a mixed primer of the following primers 22 to 38 and the following primer 39 as a sense primer and antisense primer for light chain variable region cloning, respectively.

```
[List of Primers]
Primer 1
                                       (SEQ ID NO: 30)
NNCCATGGCCGAGGTRMAGCTTCAGGAGTC Primer 2
                                       (SEQ ID NO: 31)
NNCCATGGCCGAGGTBCAGCTBCAGCAGTC Primer 3
                                       (SEQ ID NO: 32)
NNCCATGGCCGAGGTGCAGCTGAAGSASTC Primer 4
                                       (SEQ ID NO: 33)
NNCCATGGCCGAGGTCCARCTGCAACARTC Primer 5
                                       (SEQ ID NO: 34)
NNCCATGGCCGAGGTYCAGCTBCAGCARTC Primer 6
                                       (SEQ ID NO: 35)
NNCCATGGCCGAGGTYCARCTGCAGCAGTC Primer 7
                                       (SEQ ID NO: 36)
NNCCATGGCCGAGGTCCACGTGAAGCAGTC Primer 8
                                       (SEQ ID NO: 37)
NNCCATGGCCGAGGTGAASSTGGTGGAATC Primer 9
                                       (SEQ ID NO: 38)
NNCCATGGCCGAGGTGAWGYTGGTGGAGTC Primer 10
                                       (SEQ ID NO: 39)
NNCCATGGCCGAGGTGCAGSKGGTGGAGTC Primer 11
                                       (SEQ ID NO: 40)
NNCCATGGCCGAGGTGCAMCTGGTGGAGTC Primer 12
                                       (SEQ ID NO: 41)
NNCCATGGCCGAGGTGAAGCTGATGGARTC Primer 13
                                       (SEQ ID NO: 42)
NNCCATGGCCGAGGTGCARCTTGTTGAGTC Primer 14
                                       (SEQ ID NO: 43)
NNCCATGGCCGAGGTRAAGCTTCTCGAGTC Primer 15
                                       (SEQ ID NO: 44)
NNCCATGGCCGAGGTGAARSTTGAGGAGTC Primer 16
                                       (SEQ ID NO: 45)
NNCCATGGCCGAGGTTACTCTRAAAGWGTSTG Primer 17
                                       (SEQ ID NO: 46)
NNCCATGGCCGAGGTCCAACTVCAGCARCC Primer 18
                                       (SEQ ID NO: 47)
NNCCATGGCCGAGGTGAACTTGGAAGTGTC Primer 19
                                       (SEQ ID NO: 48)
NNCCATGGCCGAGGTGAAGGTCATCGAGTC Primer 20
                                       (SEQ ID NO: 49)
TGTGCAGACCCTCGTGGACCACGGAGCA Primer 21
                                       (SEQ ID NO: 50)
GGACTCTGGGRTCATTTACCMGGAGAGT Primer 22
                                       (SEQ ID NO: 51)
NNNNGTCGACGCTCGAYATCCAGCTGACTCAGCC Primer 23
                                       (SEQ ID NO: 52)
NNNNGTCGACGCTCGAYATTGTTCTCWCCCAGTC Primer 24
                                       (SEQ ID NO: 53)
NNNNGTCGACGCTCGAYATTGTGMTMACTCAGTC
```

-continued

Primer 25
(SEQ ID NO: 54)
NNNNGTCGACGCTCGAYATTGTGYTRACACAGTC

Primer 26
(SEQ ID NO: 55)
NNNNGTCGACGCTCGAYATTGTRATGACMCAGTC

Primer 27
(SEQ ID NO: 56)
NNNNGTCGACGCTCGAYATTMAGATRAMCCAGTC

Primer 28
(SEQ ID NO: 57)
NNNNGTCGACGCTCGAYATTCAGATGAYDCAGTC

Primer 29
(SEQ ID NO: 58)
NNNNGTCGACGCTCGAYATYCAGATGACACAGAC

Primer 30
(SEQ ID NO: 59)
NNNNGTCGACGCTCGAYATTGTTCTCAWCCAGTC

Primer 31
(SEQ ID NO: 60)
NNNNGTCGACGCTCGAYATTGWGCTSACCCAATC

Primer 32
(SEQ ID NO: 61)
NNNNGTCGACGCTCGAYATTSTRATGACCCARTC

Primer 33
(SEQ ID NO: 62)
NNNNGTCGACGCTCGAYRTTKTGATGACCCARAC

Primer 34
(SEQ ID NO: 63)
NNNNGTCGACGCTCGAYATTGTGATGACBCAGKC

Primer 35
(SEQ ID NO: 64)
NNNNGTCGACGCTCGAYATTGTGATAACYCAGGA

Primer 36
(SEQ ID NO: 65)
NNNNGTCGACGCTCGAYATTGTGATGACCCAGWT

Primer 37
(SEQ ID NO: 66)
NNNNGTCGACGCTCGAYATTGTGATGACACAACC

Primer 38
(SEQ ID NO: 67)
NNNNGTCGACGCTCGAYATTTTGCTGACTCAGTC

Primer 39
(SEQ ID NO: 68)
CCTTAGGAGGGAAGATTGGAAGGAGCT

It should be noted that, in the base sequences, R represents G or A, Y represents T or C, M represents A or C, K represents G or T, S represents G or C, W represents A or T, B represents G, C, or T, D represents A, G, or T, V represents A, G, or C, and N represents A, T, G, or C.

Each PCR product obtained in the foregoing was cloned into a vector to determine its base sequence in accordance with a conventional method.

The base sequences of the heavy chain variable region and the light chain variable region of the anti-hTF monoclonal antibody (No. 1849) determined as described above are set forth in SEQ ID NOS: 69 and 70, respectively. In addition, the amino acid sequences of the heavy chain variable region and the light chain variable region are set forth in SEQ ID NOS: 9 and 10, respectively. In addition, those amino acid sequences were compared to a database of the amino acid sequences of known antibodies (website of IMGT: www.imgt.org) to investigate their homologies. Thus, the amino acid sequences of the CDRs were determined to be as follows.

TABLE 1

| No. 1849 | | Amino acid sequence | SEQ ID NO: |
|---|---|---|---|
| Heavy chain variable region | CDR1 | DYNMA | 3 |
| | CDR2 | AIIYDGTRTYYRDSVRG | 4 |
| | CDR3 | GDSYTNFAY | 5 |
| Light chain variable region | CDR1 | RASSSLSYMH | 6 |
| | CDR2 | ETSKLAS | 7 |
| | CDR3 | QQGNSYPRT | 8 |

2. Anti-hTF Monoclonal Antibody (No. 1859)

The base sequences of the heavy chain variable region and the light chain variable region of the anti-hTF monoclonal antibody (No. 1859) were determined in the same manner as above except that total RNA was extracted from hybridomas producing the anti-hTF monoclonal antibody (No. 1859) and primer 21 was used as the antisense primer for the heavy chain variable region cloning.

The determined base sequences of the heavy chain variable region and the light chain variable region of the anti-hTF monoclonal antibody (No. 1859) are set forth in SEQ ID NOS: 71 and 72, respectively. In addition, the amino acid sequences of the heavy chain variable region and the light chain variable region are set forth in SEQ ID NOS: 17 and 18, respectively. In addition, the amino acid sequences of the CDRs in those variable regions were determined to be as follows.

TABLE 2

| No. 1859 | | Amino acid sequence | SEQ ID NO: |
|---|---|---|---|
| Heavy chain variable region | CDR1 | DYSVH | 11 |
| | CDR2 | VMWSGGTTTFNSGLKS | 12 |
| | CDR3 | ERAGSPLNWFAY | 13 |
| Light chain variable region | CDR1 | QASQDIGNYLS | 14 |
| | CDR2 | SSTSLAD | 15 |
| | CDR3 | LQHYSGSRT | 16 |

[Binding Activity Evaluation by Surface Plasmon Resonance Method]

The anti-hTF monoclonal antibodies (No. 1849 and No. 1859) were each immobilized on the surface of a Biacore CM5 chip. The CM5 chip, which had each antibody immobilized thereon, was set in a SPR device, and an antigen-containing buffer containing purified hTF was allowed to flow through its flow path. The dissociation constant between each of the antibodies and hTF was determined by this measurement system. It should be noted that the measurement conditions were as follows.

SPR apparatus: Biacore 2000 (Biacore)
Antibody-containing buffer: 10 mM acetate buffer (pH5.0) containing hTF at a final concentration of 25 µg/ml
Running buffer: HBS-EP buffer (10 mM HEPES, pH 7.5, 0.15 M NaCl, 3 mM EDTA, 0.005% surfactant P20 (Tween 20), pH 7.4).

As a result of the measurement, the dissociation constants (KD) between hTF and the antibodies No. 1849 and No. 1859 were $9.139 \times 10^{-11}$ and $1.894 \times 10^{-10}$, respectively.

[Anticoagulant Activity Evaluation]

The prothrombin time of each of the anti-hTF monoclonal antibodies (No. 1849 and No. 1859) was measured as described below.

3 μg of the antibody was added to 350 ng of a recombinant hTF antigen, and PBS was added to a total volume of 5 μl. An antigen-antibody reaction was performed for 15 minutes under shaking at 37° C. and 600 rpm. To the reaction solution, 50 μl of human serum subjected to anticoagulant treatment with 3.8% sodium citrate, and 100 μl of 25 mM CaCl₂ were added, and at the same time, culturing was performed under shaking at 37° C. and 600 rpm. The period of time until a fibrin clot was formed (prothrombin time) was measured. The prolonged coagulation time ratio (prothrombin time ratio) of each antibody when the prothrombin time in a control using PBS in place of the reaction solution is defined as 1 are shown in Table 3 and FIG. 2.

TABLE 3

|  | No. 1849 | No. 1859 | Control (PBS) |
|---|---|---|---|
| Prolonged coagulation time ratio | 5.535 | 1.222 | 1 |

Figure 2:
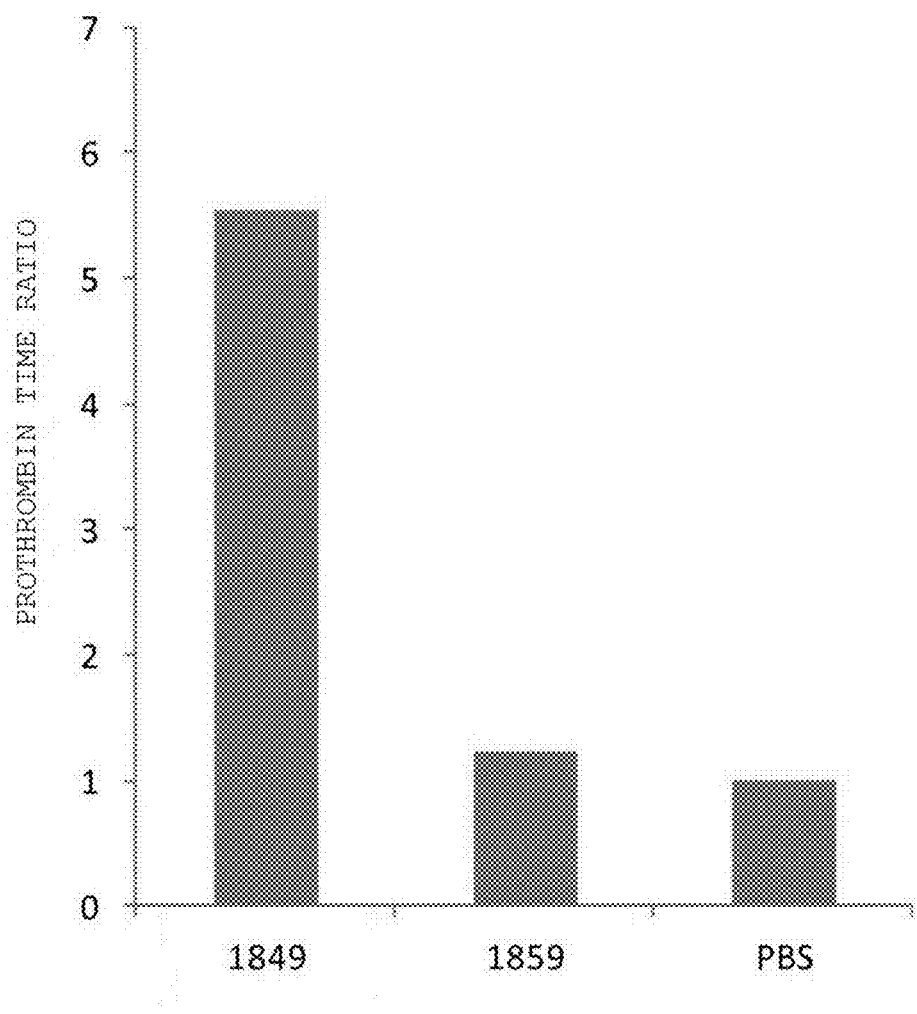
FIG. 2 is a graph that shows the results of an anticoagulant activity evaluation.

As shown in Table 3 and FIG. 2, the prolonged coagulation time ratio of No. 1859 is 1.222, and thus its anticoagulant activity was found to be extremely small.

Example 2: Pharmaceutical Composition

[Binding Between Monoclonal Antibody and Drug]

The anti-hTF monoclonal antibody (No. 1849) having monomethyl auristatin E (MMAE) bound thereto (hereinafter referred to as "hTF-MMAE") was obtained as described below.

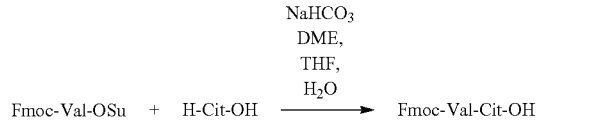

To an aqueous solution (18 mL) of H-Cit-OH (1.18 g, 6.74 mmol) and NaHCO₃ (566 mg, 6.74 mmol), a solution of Fmoc-Val-OSu (2.80 g, 6.42 mmol) in DME (18 mL) was added, and THF (9 mL) was further added. The mixture was stirred overnight. The reaction was stopped with a 15% citric acid aqueous solution (40 mL), and the aqueous layer was extracted with an AcOEt/i-PrOH (9/1) mixed solution (100 mL, 20 mL×2). The combined organic layer was washed with water (70 mL), and concentrated under reduced pressure. The residual solid was washed with diethyl ether to afford a dipeptide (3.11 g, 97%) as a white solid.

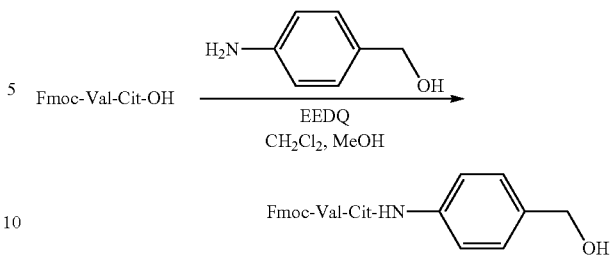

To a solution of Fmoc-Val-Cit-OH (3.00 g, 6.04 mmol) and p-aminobenzyl alcohol (1.49 g, 12.1 mmol) in dichloromethane (70 mL) and methanol (30 mL), 1-ethoxycarbonyl-2-ethoxy-1,2-dihydroquinoline (EEDQ) (2.99 g, 12.1 mmol) was added. After 1 day, EEDQ (1.50 g, 6.04 mmol) was further added, and the mixture was stirred overnight. The reaction solution was concentrated, and the residue was washed with diethyl ether to afford the target product (2.51 g, 69%).

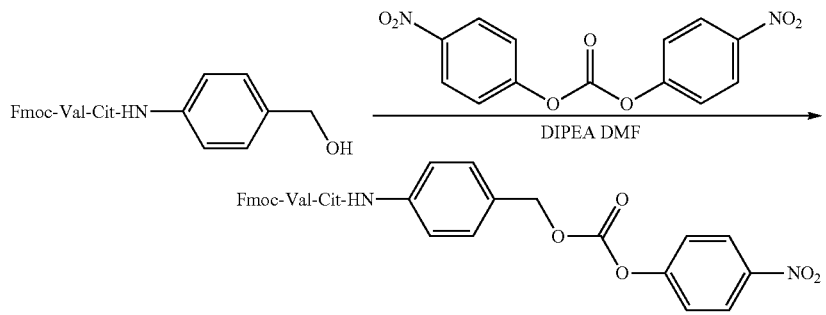

Fmoc-Val-Cit-PAB-OH (2.00 g, 3.32 mmol) was dissolved in dimethylformamide (20 mL), and bis-p-nitrophenyl carbonate (2.02 mg, 6.65 mmol) and diisopropylethylamine (0.87 mL, 4.98 mmol) were added. After stirring overnight, the reaction solution was concentrated under reduced pressure, and the residue was washed with ethyl acetate and diethyl ether to afford a p-nitrophenyl carbonate (1.73 g, 68%).

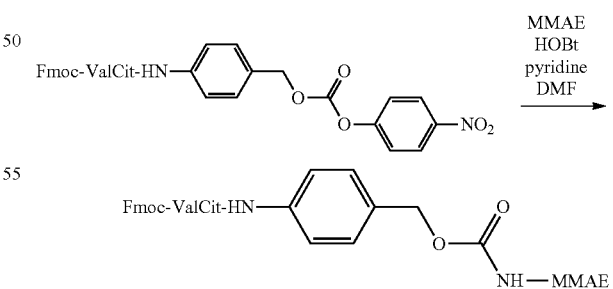

To a solution of the p-nitrophenyl carbonate (1.28 g, 1.67 mmol) and HOBt (376 mg, 2.78 mmol) in dimethylformamide (3.4 mL) and pyridine (0.85 mL), MMAE (1.00 g, 1.39 mmol) was added. After 24 hours, the reaction solution was purified with Sephadex LH20 (solvent: CHCl₃:MeOH=1:1) to afford Fmoc-Val-Cit-PABC-MMAE (1.44 g, 77%).

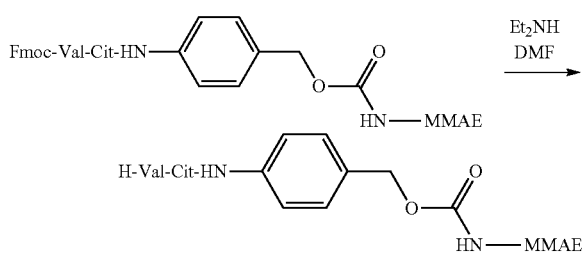

To a solution (20 mL) of Fmoc-Val-Cit-PABC-MMAE (1.44 g, 1.07 mmol) in dimethylformamide, $Et_2NH$ (5 mL) was added. After stirring overnight, the reaction solution was concentrated under reduced pressure, and the residue was washed with ethyl acetate and diethyl ether to afford a pale yellow solid (960 mg, 800).

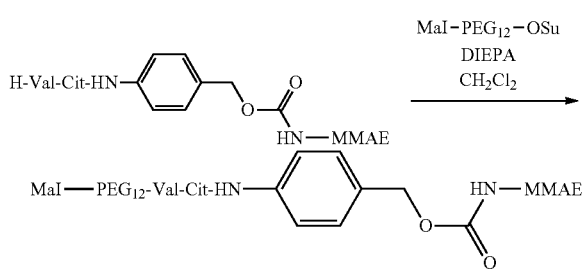

To a solution (20 mL) of H-Val-Cit-PABC-MMAE (960 mg, 0.855 mmol) in dichloromethane, Mal-PEG$_{12}$-OSu having a maleimide group at the N-terminus (814 mg, 0.94 mmol) and diisopropylethylamine (0.45 mmol, 2.57 mmol) were added. After stirring overnight, the reaction solution was purified through the use of Sephadex LH20 (CHCl$_3$: MeOH=1:1) and gel filtration HPLC to afford Mal-PEG$_{12}$-Val-Cit-PABC-MMAE (hereinafter sometimes referred to as "maleimide MMAE compound") as a colorless oil (769 mg, 48%).

A buffer having a pH of 6.4 was prepared using 5 mM EDTA-containing PBS, and a 150 mM NaCl and 5 mM EDTA-containing 100 mM phosphate buffer (pH 6.0), and an antibody solution was prepared with the resultant buffer to have an antibody concentration of 1.0 mg/ml. To the antibody solution, dithiothreitol (DTT) was added to have a final concentration of from 1 mM to 10 mM, and the mixture was allowed to react at from 26° C. to 37° C. for from 30 minutes to 45 minutes. Then, Amicon® Ultra (MWCO: 30,000) was used to remove the reaction reagent from the reaction solution. Absorption was measured, and the recovery ratio of the antibody was found to be from 80% to 99%. In addition, the result of quantification of SH groups based on 5,5'-dithiobis(2-nitrobenzoic acid) (DNTB) revealed that three to five SH groups were obtained per antibody.

Next, a buffer having a pH of 6.4 was prepared using 5 mM EDTA-containing PBS, and a 150 mM NaCl and 5 mM EDTA-containing 100 mM phosphate buffer (pH 6.0), and the reaction solution was diluted with the resultant buffer to have a protein concentration of 0.5 mg/ml. The diluted solution was mixed with the maleimide MMAE compound at a molar ratio of 1:4 (antibody:maleimide MMAE compound), and the resultant was allowed to react at room temperature for 1 hour and then at 4° C. overnight.

After that, Amicon® Ultra (MWCO: 30,000) was used to remove the reaction reagent from the reaction solution, and then the solvent was replaced with PBS. A protein was recovered with Amicon® Ultra, and the recovery ratio was from 60% to 90%.

Thus, hTF-MMAE having three to five MMAE molecules added per antibody was obtained.

[Cytocidal Effect Confirmation Test]

Human pancreatic cancer cells (BxPC3) were added to a 96-well plate at 3×10$^3$ cells/well, and cultured in RPMI medium containing 10% FCS, penicillin (100 U/ml), and streptomycin (100 µg/ml) hTF-MMAE was added to the wells at various drug concentrations, and cell survival rates 72 hours after the addition were calculated.

It should be noted that, as a comparative test, a similar test was performed using, in place of hTF-MMAE, mTF-MMAE obtained by binding MMAE, in the same manner as above, to a monoclonal antibody (mTF) against mouse TF not expressed in human cancer cells, and a cell survival rate was calculated. The ratio (%) of each cell survival rate, with the cell survival rate of a negative control (no addition of a drug sample) being defined as 100%, is shown in FIG. 3.

Figure 3:
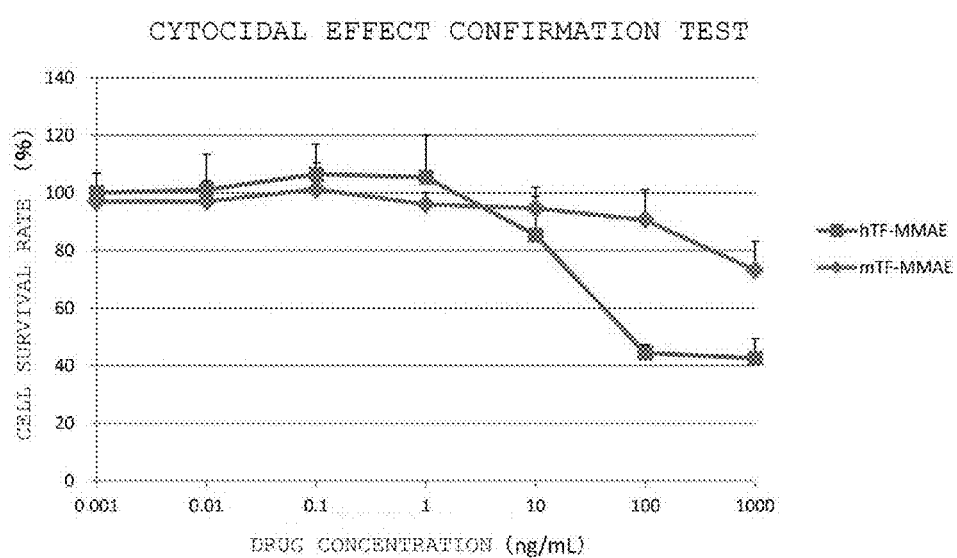
FIG. 3 is a graph that shows the results of a cytocidal effect confirmation test.

As shown in FIG. 3, hTF-MMAE showed a remarkably excellent cytocidal effect as compared to mTF-MMAE. This indicates that, when a drug is bound to the anti-hTF monoclonal antibody (No. 1849), its property of being transferred into a cell expressing hTF at its surface can be improved to allow high efficacy of the drug to be exhibited.

[Antitumor Effect Confirmation Test]

1×10$^7$ cells/100 µL of human pancreatic cancer cells (BxPC3) were implanted subcutaneously into the backs of 4-week-old nude mice (BALBc nu/nu, female), and treatment was initiated when the tumor volume (calculated based on the tumor diameter) reached about 200 mm$^3$. The day of initiation of the treatment was defined as Day 0, and a drug was administered to the tail vein once on each of Day 0, Day 4, and Day 8 (administration three times in total). hTF-MMAE was used as the drug, and physiological saline was administered as a control (each group: N=7). The dose of the drug was 10 mg/kg per administration (antibody amount: about 200 µg/mouse). Thereafter, the tumor diameter and the body weight were measured twice a week until Day 30. The ratios of the tumor volume and the body weight to the tumor volume and the body weight at Day 0 are shown in FIG. 4 and FIG. 5, respectively.

Figure 4:
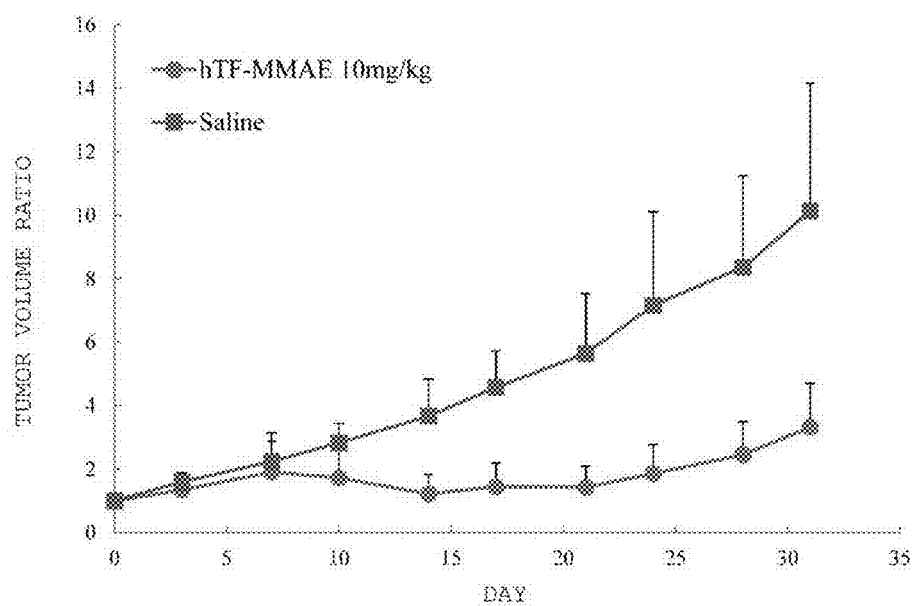
FIG. 4 is a graph that shows changes in tumor volume in an antitumor effect confirmation test.
Figure 5:
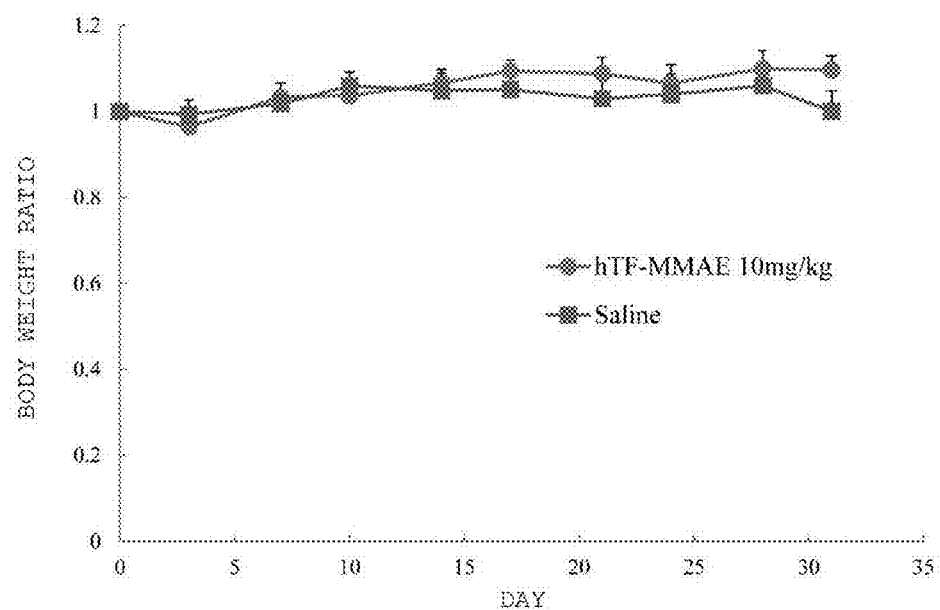
FIG. 5 is a graph that shows changes in body weight in the antitumor effect confirmation test.

As shown in FIG. 4, hTF-MMAE showed a remarkably excellent antitumor effect. The result agrees with the cytocidal effect confirmed in vitro. In addition, as shown in FIG. 5, a reduction in body weight was not found in the group to which hTF-MMAE had been administered.

Example 3: Anti-mTF Monoclonal Antibody and Fragment Thereof

[Preparation of Antigen]

A recombinant protein containing an amino acid sequence from position 30 to position 251 in the full-length amino acid sequence of mTF was expressed using *Escherichia coli*, and purified with a nickel column to afford recombinant mTF (SEQ ID NO: 73), which was used as the antigen.

[Immunization of Rats]

50 µg of the recombinant mTF was intraperitoneally coadministered with Freund's complete adjuvant (Difco) to three 6-week-old Wistar female rats and thus initial immunization was performed. After 14 days therefrom, 50 µg of the recombinant mTF was coadministered with Sigma Adjuvant System® (Sigma) and thus a booster immunization was performed. Thereafter, similar booster immunizations were performed every 21 days seven times. After an additional 207 days, 10 μg of the recombinant mTF diluted with PBS was intraperitoneally administered and 40 μg of the recombinant mTF was administered to the tail vein; thus, final immunization was performed.

[Preparation of Hybridomas]

After 3 days from the final immunization, the spleen was excised, and spleen cells were collected. The spleen cells and mouse myeloma cells (p3X63Ag8.653) were fused using polyethylene glycol 4000 (Merck) at a concentration of 50%, and selection was performed in HAT medium.

[Screening of Antibody-Producing Hybridomas]

After 8 days from the cell fusion, screening of antibody-producing hybridomas was performed. The immunoassay used for the screening is the following. For an ELISA method, a 50 mM carbonate buffer (pH 8) containing 1 μg/mL of the recombinant mTF was added to each well of a 96-well microtiter plate (manufactured by Nunc) at 50 μL/well, and immobilization was performed at 4° C. overnight or at room temperature for 2 hours. The wells were washed three times with 300 μL of a washing solution (0.05% Tween 20/25 mM Tris/140 mM NaCl/2.5 mM KCl, pH 7.4), and then 200 μL of a blocking buffer (0.05% Tween 20/1% BSA/100 mM $NaH_2PO_4$/140 mM NaCl, pH 5) was added, followed by standing at 4° C. overnight or at room temperature for 1 hour to undergo blocking. 50 μL of a hybridoma culture supernatant was added to each well of the thus-obtained mTF-immobilized plate and the mixture was allowed to react at room temperature for 1 hour. Each well was washed three times with 300 μL of the washing solution, and then 50 μL of an HRP-labeled anti-mouse IgG antibody (Bethyl) diluted 5,000-fold with the blocking buffer was added, and the mixture was allowed to react for 30 minutes. After the reaction, each well was washed three times with 300 μL of the washing solution, and 100 μL of 3.7 mM o-phenylenediamine/25 mM citric acid/130 mM $Na_2HPO_4$/0.006% $H_2O_2$ (pH 5.0) was added to develop a color. After from 10 minutes to 15 minutes, 2 N sulfuric acid was added at 30 μL/well to stop the reaction, and absorbance (490 nM) was measured with an absorbance plate reader. In addition, an immunoprecipitation ELISA method was performed by mixing the recombinant mTF and the hybridoma culture supernatant, and measuring the amount of unbound mTF in the mixed liquid using an mTF-quantifying sandwich ELISA. Further, a flow cytometry method was performed in accordance with a conventional method to measure the reactivity of the hybridoma culture supernatant to mTF-expressing cells.

Hybridomas that showed a strong affinity for mTF as a result of the measurement were selected, and a limiting dilution method was performed twice for clones of the hybridomas to establish hybridoma clones producing monoclonal antibodies that bind to mTF.

[Preparation of Antibodies]

Each established hybridoma was mass-cultured in, for example, RPMI 1640 medium containing bovine serum in an amount of 5% having removed therefrom IgG of bovine origin, to afford a culture supernatant. Alternatively, each hybridoma was mass-cultured in the abdominal cavity of ICR nude mice, and peritoneal fluid was collected. The resultant culture supernatant or peritoneal fluid was subjected to Protein G affinity column chromatography to purify IgG monoclonal antibodies.

[Internalization Assay]

Each monoclonal antibody obtained as described above was subjected to the following internalization assay.

Mouse B16 melanoma cells and cells thereof that were forced to express TF were seeded into a four-chamber Culture Slide (BD) at $5\times10^4$ cells/chamber, and cultured in RPMI 1640 medium at 37° C. under a 5% $CO_2$ environment for 12 hours. The resultant was washed three times with PBS, and then 30 μg of antibody labeled with an Alexa 647 fluorescence labeling kit (Invitrogen) was diluted with 1 ml of RPMI 1640 medium and added to each chamber, followed by culturing for 3 hours. After 2 hours from the initiation of this culturing, Lysotracker® RED-DND99 (Invitrogen) was added to the culture solution to have a final concentration of 75 nM, followed by further culturing for 1 hour. Then, the resultant was washed three times with PBS. After that, immobilization was performed with 4% paraformaldehyde, and nuclear staining was performed with 4',6-diamidino-2-phenylindole (DAPI), followed by mounting with Fluoromount-G® (Southern Biotech). Then, the cells were observed using a fluorescence microscope (Keyence). The result of the observation is shown in FIG. 6.

Figure 6:
FIG. 6 is a micrograph that shows the result of an internalization assay.
Figure 7:
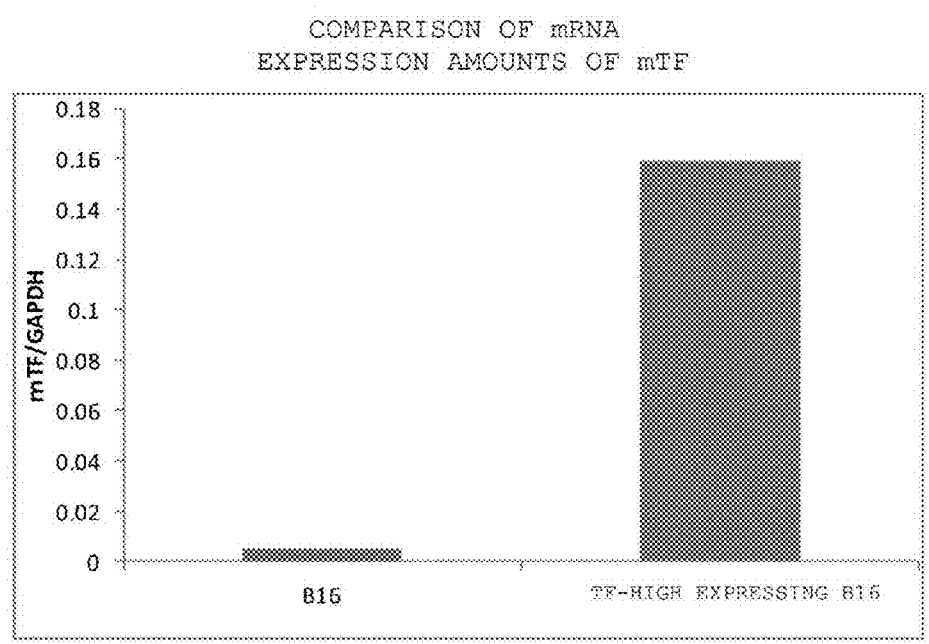
FIG. 7 is a graph that shows the ratios of mRNA expression amounts of TF to mRNA expression amounts of GAPDH in mouse B16 melanoma cells and TF forced-expression cells thereof.

As shown in FIG. 6, in one monoclonal antibody (No. 1157), the fluorescence-labeled antibody (red) transferred into cells, and thus it was confirmed that the monoclonal antibody had the ability to be internalized by a cell expressing mTF. It should be noted that, in FIG. 6, cells into which the fluorescence-labeled antibody (red) transferred were presumed to be the TF-forced-expression mouse B16 melanoma cells and cells into which the antibody did not transfer were presumed to be the normal mouse B16 melanoma cells (for reference, the enhancement level of the TF expression amount in the TF-forced-expression mouse B16 melanoma cells is shown in FIG. 7. FIG. 7 is a graph that shows the ratios of the mRNA expression amounts of TF to the mRNA expression amounts of GAPDH in the mouse B16 melanoma cells and the TF-forced-expression cells thereof).

[Determination of DNA Sequence Encoding Variable Regions, Amino Acid Sequences, and CDR Sequences]

The base sequences of the heavy chain variable region and the light chain variable region of the anti-mTF monoclonal antibody (No. 1157) were determined in the same manner as in the method of determining the base sequences of the heavy chain variable region and the light chain variable region of the anti-hTF monoclonal antibody (No. 1849) except that total RNA was extracted from hybridomas producing the anti-mTF monoclonal antibody (No. 1157).

The determined base sequences of the heavy chain variable region and the light chain variable region of the anti-mTF monoclonal antibody (No. 1157) are set forth in SEQ ID NOS: 74 and 75, respectively. In addition, the amino acid sequences of the heavy chain variable region and the light chain variable region are set forth in SEQ ID NOS: 25 and 26, respectively. In addition, the amino acid sequences of the CDRs in those variable regions were determined to be as follows.

TABLE 4

| No. 1157 | | Amino acid sequence | SEQ ID NO: |
|---|---|---|---|
| Heavy chain variable region | CDR1 | TDYGM | 19 |
| | CDR2 | SITVRNYIYYADTVK | 20 |
| | CDR3 | RTEGMDY | 21 |
| Light chain variable region | CDR1 | KVSQNINGYLN | 22 |
| | CDR2 | NTDNLQT | 23 |
| | CDR3 | LQHYSWPLT | 24 |

Example 4: Production of Chimeric Antibodies

DNA fragments encoding the heavy chain variable region and the light chain variable region of the anti-hTF monoclonal antibody (No. 1849) cloned in Example 1 were amplified by PCR. The DNA fragment for the heavy chain variable region was inserted into a human IgG1 heavy chain constant region-expressing cloning vector (pFUSEss_CHIg-hG1e2 (invivoGen)) and the DNA fragment for the light chain variable region was inserted into a human kappa light chain constant region-expressing cloning vector (pFUSE2ss_CLIg_hk (invivoGen)) to afford expression vectors. The resultant expression vectors were transfected into CHO-K1 cells using Lipofectamine® LTX Reagent (Invitrogen). Then, drug selection was performed with 10 μg/mL of Blastcidin S (Kaken Pharmaceutical Co., Ltd.) and 300 μg/mL of Zeocin™ (Invitrogen) to afford a double-resistant cell line.

The resultant cell line was maintained and cultured in a medium containing Ham's F12K (Wako), 10% FBS, 1% penicillin, streptomycin (Invitrogen), 10 μg/mL of Blastcidin S, and 300 μg/mL of Zeocin. Then, a constitutively anti-hTF human chimeric antibody-expressing cell line (No. 1849 chimeric clone) was cloned by a limiting dilution method that involved using a 96-well plate.

Figure 8:
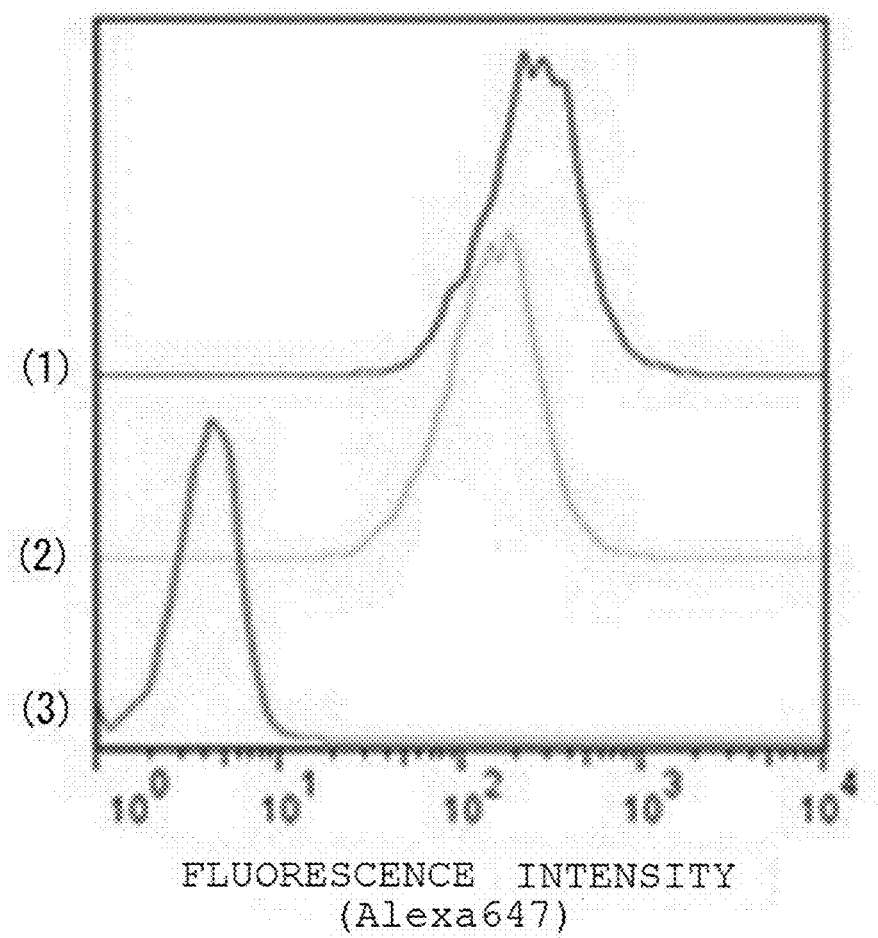
FIG. 8 is a histogram obtained by FACS analysis.

The culture supernatant of the cloned cell line (No. 1849 chimeric clone) was subjected to ELISA, and as a result, reactivity to hTF was able to be confirmed. In addition, the culture supernatant of the cloned cell line was subjected to flow cytometry analysis (FACS), and as a result, reactivity to human colon adenocarcinoma cells (DLD-1) was able to be confirmed. Specifically, as shown in FIG. 8, the culture supernatant showed specific reactivity to hTF-expressing cells DLD-1 (in FIG. 8, (1), (2), and (3) indicate analysis results using the rat anti-hTF monoclonal antibody (No. 1849), the culture supernatant of the No. 1849 chimeric clone, and a rat isotype control, respectively).

[Determination of DNA Sequences Encoding Chimeric Antibody and Amino Acid Sequences]

A vector was extracted from the No. 1849 chimeric clone, and the base sequences and the amino acid sequences of the heavy chain and the light chain of the anti-hTF human chimeric antibody (No. 1849) encoded by the vector were determined in accordance with a conventional method. The determined base sequences of the heavy chain and the light chain of the chimeric antibody are set forth in SEQ ID NOS: 76 and 77, respectively. In addition, the determined amino acid sequences of the heavy chain and the light chain of the chimeric antibody are set forth in SEQ ID NOS: 78 and 79, respectively.

Monoclonal antibodies or fragments thereof of the present invention can be suitably utilized in the field of DDS.

---

The invention claimed is:

1. A monoclonal antibody or biologically active fragment thereof, which binds to tissue factor, selected from the group consisting of:

an anti-human tissue factor monoclonal antibody or biologically active fragment thereof including a heavy chain variable region having complementarity determining regions 1, 2, and 3 containing the amino acid sequences set forth in SEQ ID NOS: 3, 4, and 5, respectively, and a light chain variable region having complementarity determining regions 1, 2, and 3 containing the amino acid sequences set forth in represented by SEQ ID NOS: 6, 7, and 8, respectively; and an anti-human tissue factor monoclonal antibody or biologically active fragment thereof including a heavy chain variable region having complementarity determining regions 1, 2, and 3 containing the amino acid sequences set forth in represented by SEQ ID NOS: 11, 12, and 13, respectively, and a light chain variable region having complementarity determining regions 1, 2, and 3 containing the amino acid sequences set forth in represented by SEQ ID NOS: 14, 15, and 16, respectively.

2. The monoclonal antibody according to claim 1, selected from the group consisting of:

an anti-human tissue factor monoclonal antibody or biologically active fragment thereof including a heavy chain variable region containing the amino acid sequence set forth in SEQ ID NO: 9 or an amino acid sequence which is 90% or more identical to the amino acid sequence set forth in SEQ ID NO: 9, and a light chain variable region containing the amino acid sequence set forth in SEQ ID NO: 10 or an amino acid sequence which is 90% or more identical to the amino acid sequence set forth in SEQ ID NO: 10; and an anti-human tissue factor monoclonal antibody or biologically active fragment thereof including a heavy chain variable region containing the amino acid sequence set forth in SEQ ID NO: 17 or an amino acid sequence which is 90% or more identical to the amino acid sequence set forth in SEQ ID NO: 17, and a light chain variable region containing the amino acid sequence set forth in SEQ ID NO: 18 or an amino acid sequence which is 90% or more identical to the amino acid sequence set forth in SEQ ID NO: 18.

3. The monoclonal antibody according to claim 1, wherein the monoclonal antibody is a human chimeric antibody or a humanized antibody.

4. A pharmaceutical composition, comprising:
the monoclonal antibody or biologically active fragment thereof of claim 1 as a target-binding factor; and
a drug.

5. A composition for drug delivery, comprising the monoclonal antibody or biologically active fragment thereof of claim 1 as a target-binding factor.

6. A pharmaceutical composition, comprising:
the monoclonal antibody or biologically active fragment thereof of claim 2 as a target-binding factor; and
a drug.

7. A composition for drug delivery, comprising the monoclonal antibody or biologically active fragment thereof of claim 2 as a target-binding factor.

8. An isolated nucleic acid sequence encoding an antibody or biologically active fragment thereof comprising the heavy chain CDR sequences and light chain CDR sequences according to claim 1.

9. An isolated nucleic acid sequence encoding an antibody or antigen-binding fragment thereof according to claim 2.

10. An expression vector comprising the nucleic acid sequence of claim 8.

11. An expression vector comprising the nucleic acid sequence of claim 9.

12. A host cell comprising the vector of claim 10.

13. A host cell comprising the vector of claim 11.

14. A method for treating cancer, inflammation, or thrombosis, comprising administering to a patient in need thereof the monoclonal antibody or biologically active fragment thereof according to claim 1 bound to a drug effective for treating cancer, inflammation, or thrombosis.

15. A method for treating cancer, inflammation, or thrombosis, comprising administering to a patient in need thereof the monoclonal antibody or biologically active fragment thereof according to claim 2 bound to a drug effective for treating cancer, inflammation, or thrombosis.

16. A method for treating cancer, inflammation, or thrombosis, comprising administering to a patient in need thereof the pharmaceutical composition according to claim wherein the drug is effective for treating cancer, inflammation, or thrombosis and wherein the drug is bound to the monoclonal antibody or biologically active fragment thereof.

17. A method for treating cancer, inflammation, or thrombosis, comprising administering to a patient in need thereof the pharmaceutical composition according to claim 4, wherein the drug is effective for treating cancer, inflammation, or thrombosis and wherein the drug is bound to the monoclonal antibody or biologically active fragment thereof.

18. The method for treating cancer, inflammation, or thrombosis according to claim 14, wherein the monoclonal antibody or biologically active fragment thereof binds to tissue factor at a dissociation constant (KD) of $2 \times 10^{-10}$ M or less.

19. The monoclonal antibody or biologically active fragment thereof according to claim 1, wherein the monoclonal antibody or biologically active fragment thereof binds to tissue factor at a dissociation constant (KD) of $2 \times 10^{-10}$ M or less.

* * * * *

UNITED STATES PATENT AND TRADEMARK OFFICE
CERTIFICATE OF CORRECTION

PATENT NO. : 9,920,133 B2
APPLICATION NO. : 15/111875
DATED : March 20, 2018
INVENTOR(S) : Yasuhiro Matsumura et al.

Page 1 of 1

It is certified that error appears in the above-identified patent and that said Letters Patent is hereby corrected as shown below:

In the Claims

In Claim 16, at Column 72, Line 5, add "4" after "the pharmaceutical composition according to claim".

In Claim 17, at Column 72, Line 12, replace "claim 4" with "claim 6".

Signed and Sealed this
Twenty-ninth Day of May, 2018

Andrei Iancu
*Director of the United States Patent and Trademark Office*

SEQUENCE LISTING

<160> NUMBER OF SEQ ID NOS: 79

<210> SEQ ID NO 1
<211> LENGTH: 295
<212> TYPE: PRT
<213> ORGANISM: human

<400> SEQUENCE: 1

```
Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205
```

```
Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Ile Ile Leu Val Ile Ile Leu Ala Ile
                260                 265                 270

Ser Leu His Lys Cys Arg Lys Ala Gly Val Gly Gln Ser Trp Lys Glu
                275                 280                 285

Asn Ser Pro Leu Asn Val Ser
    290                 295

<210> SEQ ID NO 2
<211> LENGTH: 294
<212> TYPE: PRT
<213> ORGANISM: mouse

<400> SEQUENCE: 2

Met Ala Ile Leu Val Arg Pro Arg Leu Leu Ala Ala Leu Ala Pro Thr
1               5                   10                  15

Phe Leu Gly Cys Leu Leu Gln Val Thr Ala Gly Ala Gly Ile Pro
                20                  25                  30

Glu Lys Ala Phe Asn Leu Thr Trp Ile Ser Thr Asp Phe Lys Thr Ile
                35                  40                  45

Leu Glu Trp Gln Pro Lys Pro Thr Asn Tyr Thr Tyr Thr Val Gln Ile
50                  55                  60

Ser Asp Arg Ser Arg Asn Trp Lys Asn Lys Cys Phe Ser Thr Thr Asp
65                  70                  75                  80

Thr Glu Cys Asp Leu Thr Asp Glu Ile Val Lys Asp Val Thr Trp Ala
                85                  90                  95

Tyr Glu Ala Lys Val Leu Ser Val Pro Arg Arg Asn Ser Val His Gly
                100                 105                 110

Asp Gly Asp Gln Leu Val Ile His Gly Glu Glu Pro Pro Phe Thr Asn
                115                 120                 125

Ala Pro Lys Phe Leu Pro Tyr Arg Asp Thr Asn Leu Gly Gln Pro Val
                130                 135                 140

Ile Gln Gln Phe Glu Gln Asp Gly Arg Lys Leu Asn Val Val Val Lys
145                 150                 155                 160

Asp Ser Leu Thr Leu Val Arg Lys Asn Gly Thr Phe Leu Thr Leu Arg
                165                 170                 175

Gln Val Phe Gly Lys Asp Leu Gly Tyr Ile Ile Thr Tyr Arg Lys Gly
                180                 185                 190

Ser Ser Thr Gly Lys Lys Thr Asn Ile Thr Asn Thr Asn Glu Phe Ser
                195                 200                 205

Ile Asp Val Glu Glu Gly Val Ser Tyr Cys Phe Phe Val Gln Ala Met
    210                 215                 220

Ile Phe Ser Arg Lys Thr Asn Gln Asn Ser Pro Gly Ser Ser Thr Val
225                 230                 235                 240

Cys Thr Glu Gln Trp Lys Ser Phe Leu Gly Thr Leu Ile Ile Val
                245                 250                 255

Gly Ala Val Val Leu Leu Ala Thr Ile Phe Ile Ile Leu Leu Ser Ile
                260                 265                 270

Ser Leu Cys Lys Arg Arg Lys Asn Arg Ala Gly Gln Lys Gly Lys Asn
```

```
                275                 280                 285

Thr Pro Ser Arg Leu Ala
    290

<210> SEQ ID NO 3
<211> LENGTH: 5
<212> TYPE: PRT
<213> ORGANISM: rat

<400> SEQUENCE: 3

Asp Tyr Asn Met Ala
1               5

<210> SEQ ID NO 4
<211> LENGTH: 17
<212> TYPE: PRT
<213> ORGANISM: rat

<400> SEQUENCE: 4

Ala Ile Ile Tyr Asp Gly Thr Arg Thr Tyr Tyr Arg Asp Ser Val Arg
1               5                   10                  15

Gly

<210> SEQ ID NO 5
<211> LENGTH: 9
<212> TYPE: PRT
<213> ORGANISM: rat

<400> SEQUENCE: 5

Gly Asp Ser Tyr Thr Asn Phe Ala Tyr
1               5

<210> SEQ ID NO 6
<211> LENGTH: 10
<212> TYPE: PRT
<213> ORGANISM: rat

<400> SEQUENCE: 6

Arg Ala Ser Ser Ser Leu Ser Tyr Met His
1               5                   10

<210> SEQ ID NO 7
<211> LENGTH: 7
<212> TYPE: PRT
<213> ORGANISM: rat

<400> SEQUENCE: 7

Glu Thr Ser Lys Leu Ala Ser
1               5

<210> SEQ ID NO 8
<211> LENGTH: 9
<212> TYPE: PRT
<213> ORGANISM: rat

<400> SEQUENCE: 8

Gln Gln Gly Asn Ser Tyr Pro Arg Thr
1               5

<210> SEQ ID NO 9
<211> LENGTH: 118
<212> TYPE: PRT
<213> ORGANISM: rat
```

<400> SEQUENCE: 9

Glu Val Gln Leu Val Glu Ser Gly Gly Gly Leu Val Gln Ser Gly Arg
1               5                   10                  15

Ser Leu Lys Leu Ser Cys Ala Ala Ser Gly Phe Thr Phe Ser Asp Tyr
            20                  25                  30

Asn Met Ala Trp Ile Arg Gln Ala Pro Lys Lys Gly Leu Glu Trp Val
        35                  40                  45

Ala Ala Ile Ile Tyr Asp Gly Thr Arg Thr Tyr Tyr Arg Asp Ser Val
50                  55                  60

Arg Gly Arg Phe Thr Ile Ser Arg Asp Asn Ala Lys Ser Thr Leu Tyr
65                  70                  75                  80

Leu Gln Val Asp Ser Leu Arg Ser Glu Asp Thr Ala Thr Tyr Tyr Cys
                85                  90                  95

Ala Thr Gly Asp Ser Tyr Thr Asn Phe Ala Tyr Trp Gly Gln Gly Thr
            100                 105                 110

Leu Val Thr Val Ser Ser
        115

<210> SEQ ID NO 10
<211> LENGTH: 106
<212> TYPE: PRT
<213> ORGANISM: rat

<400> SEQUENCE: 10

Glu Ile Val Leu Thr Gln Ser Pro Thr Thr Met Ala Ala Ser Pro Gly
1               5                   10                  15

Glu Lys Val Thr Leu Thr Cys Arg Ala Ser Ser Ser Leu Ser Tyr Met
            20                  25                  30

His Trp Tyr Gln Gln Arg Ser Gly Thr Ser Pro Lys Leu Trp Ile Tyr
        35                  40                  45

Glu Thr Ser Lys Leu Ala Ser Gly Val Pro Asn Arg Phe Ser Gly Ser
50                  55                  60

Gly Ser Gly Thr Ser Phe Ser Leu Thr Ile Asp Ser Met Glu Thr Glu
65                  70                  75                  80

Asp Ala Ala Thr Tyr Tyr Cys Gln Gln Gly Asn Ser Tyr Pro Arg Thr
                85                  90                  95

Phe Gly Gly Gly Thr Lys Leu Glu Leu Lys
            100                 105

<210> SEQ ID NO 11
<211> LENGTH: 5
<212> TYPE: PRT
<213> ORGANISM: rat

<400> SEQUENCE: 11

Asp Tyr Ser Val His
1               5

<210> SEQ ID NO 12
<211> LENGTH: 16
<212> TYPE: PRT
<213> ORGANISM: rat

<400> SEQUENCE: 12

Val Met Trp Ser Gly Gly Thr Thr Phe Asn Ser Gly Leu Lys Ser
1               5                   10                  15

<210> SEQ ID NO 13

```
<211> LENGTH: 12
<212> TYPE: PRT
<213> ORGANISM: rat

<400> SEQUENCE: 13

Glu Arg Ala Gly Ser Pro Leu Asn Trp Phe Ala Tyr
1               5                   10

<210> SEQ ID NO 14
<211> LENGTH: 11
<212> TYPE: PRT
<213> ORGANISM: rat

<400> SEQUENCE: 14

Gln Ala Ser Gln Asp Ile Gly Asn Tyr Leu Ser
1               5                   10

<210> SEQ ID NO 15
<211> LENGTH: 7
<212> TYPE: PRT
<213> ORGANISM: rat

<400> SEQUENCE: 15

Ser Ser Thr Ser Leu Ala Asp
1               5

<210> SEQ ID NO 16
<211> LENGTH: 9
<212> TYPE: PRT
<213> ORGANISM: rat

<400> SEQUENCE: 16

Leu Gln His Tyr Ser Gly Ser Arg Thr
1               5

<210> SEQ ID NO 17
<211> LENGTH: 120
<212> TYPE: PRT
<213> ORGANISM: rat

<400> SEQUENCE: 17

Glu Val Met Leu Val Glu Ser Gly Pro Gly Leu Val Gln Pro Ser Gln
1               5                   10                  15

Thr Leu Ser Leu Ile Cys Thr Val Ser Gly Phe Ser Leu Thr Asp Tyr
            20                  25                  30

Ser Val His Trp Val Arg Gln Pro Pro Gly Lys Gly Leu Glu Trp Val
        35                  40                  45

Gly Val Met Trp Ser Gly Gly Thr Thr Phe Asn Ser Gly Leu Lys
    50                  55                  60

Ser Arg Leu Ser Ile Ser Arg Asp Thr Ser Lys Ser Gln Val Phe Leu
65                  70                  75                  80

Lys Met Tyr Ser Leu Arg Thr Glu Asp Thr Ala Val Tyr Tyr Cys Thr
                85                  90                  95

Arg Glu Arg Ala Gly Ser Pro Leu Asn Trp Phe Ala Tyr Trp Gly Gln
            100                 105                 110

Gly Thr Leu Val Thr Val Ser Ser
        115                 120

<210> SEQ ID NO 18
<211> LENGTH: 107
<212> TYPE: PRT
<213> ORGANISM: rat
```

<400> SEQUENCE: 18

Asp Ile Val Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Tyr
            20                  25                  30

Leu Ser Trp Tyr Gln Gln Lys Pro Gly Lys Ser Pro His Leu Leu Ile
        35                  40                  45

His Ser Ser Thr Ser Leu Ala Asp Gly Val Pro Ser Arg Phe Ser Gly
    50                  55                  60

Ser Arg Ser Gly Thr Gln Tyr Ser Leu Lys Ile Asn Arg Leu Gln Val
65                  70                  75                  80

Glu Asp Thr Gly Val Tyr Tyr Cys Leu Gln His Tyr Ser Gly Ser Arg
                85                  90                  95

Thr Phe Gly Gly Gly Thr Asn Leu Glu Leu Lys
            100                 105

<210> SEQ ID NO 19
<211> LENGTH: 5
<212> TYPE: PRT
<213> ORGANISM: rat

<400> SEQUENCE: 19

Thr Asp Tyr Gly Met
1               5

<210> SEQ ID NO 20
<211> LENGTH: 15
<212> TYPE: PRT
<213> ORGANISM: rat

<400> SEQUENCE: 20

Ser Ile Thr Val Arg Asn Tyr Ile Tyr Tyr Ala Asp Thr Val Lys
1               5                   10                  15

<210> SEQ ID NO 21
<211> LENGTH: 7
<212> TYPE: PRT
<213> ORGANISM: rat

<400> SEQUENCE: 21

Arg Thr Glu Gly Met Asp Tyr
1               5

<210> SEQ ID NO 22
<211> LENGTH: 11
<212> TYPE: PRT
<213> ORGANISM: rat

<400> SEQUENCE: 22

Lys Val Ser Gln Asn Ile Asn Gly Tyr Leu Asn
1               5                   10

<210> SEQ ID NO 23
<211> LENGTH: 7
<212> TYPE: PRT
<213> ORGANISM: rat

<400> SEQUENCE: 23

Asn Thr Asp Asn Leu Gln Thr
1               5

```
<210> SEQ ID NO 24
<211> LENGTH: 9
<212> TYPE: PRT
<213> ORGANISM: rat

<400> SEQUENCE: 24

Leu Gln His Tyr Ser Trp Pro Leu Thr
1               5

<210> SEQ ID NO 25
<211> LENGTH: 117
<212> TYPE: PRT
<213> ORGANISM: rat

<400> SEQUENCE: 25

Met Ala Glu Val Met Leu Val Glu Ser Gly Gly Gly Leu Val Gln Pro
1               5                   10                  15

Gly Arg Ser Leu Lys Leu Ser Cys Leu Ala Ser Gly Phe Thr Phe Thr
            20                  25                  30

Asp Tyr Gly Met Asn Trp Ile Arg Gln Thr Pro Gly Lys Gly Leu Glu
        35                  40                  45

Trp Val Ala Ser Ile Thr Val Arg Asn Tyr Ile Tyr Tyr Ala Asp Thr
50                  55                  60

Val Lys Gly Arg Phe Thr Ile Ser Arg Glu Asn Ala Lys Asn Thr Leu
65                  70                  75                  80

Tyr Leu Gln Met Thr Ser Leu Thr Ser Glu Asp Thr Ala Leu Tyr Tyr
                85                  90                  95

Cys Ser Arg Arg Thr Glu Gly Met Asp Tyr Trp Gly Gln Gly Val Met
            100                 105                 110

Val Thr Val Ser Ser
        115

<210> SEQ ID NO 26
<211> LENGTH: 105
<212> TYPE: PRT
<213> ORGANISM: rat

<400> SEQUENCE: 26

Met Thr Gln Ser Pro Ser Phe Leu Ser Ala Ser Val Gly Asp Arg Val
1               5                   10                  15

Thr Val Thr Cys Lys Val Ser Gln Asn Ile Asn Gly Tyr Leu Asn Trp
            20                  25                  30

Tyr Gln Gln Lys Val Gly Glu Ala Pro Lys Val Leu Ile Tyr Asn Thr
        35                  40                  45

Asp Asn Leu Gln Thr Asp Val Pro Ser Arg Phe Ser Gly Ser Gly Ser
    50                  55                  60

Gly Thr Val Phe Thr Leu Thr Ile Ser Ser Leu His Pro Glu Asp Val
65                  70                  75                  80

Ala Thr His Phe Cys Leu Gln His Tyr Ser Trp Pro Leu Thr Phe Gly
                85                  90                  95

Ser Gly Thr Gln Leu Glu Ile Lys Arg
            100                 105

<210> SEQ ID NO 27
<211> LENGTH: 885
<212> TYPE: RNA
<213> ORGANISM: human

<400> SEQUENCE: 27
```

```
auggagaccc cugccuggcc ccgggucccg cgccccgaga ccgccgucgc ucggacgcuc    60
cugcucggcu ggucuucgc ccaggguggcc ggcgcuucag gcacuacaaa uacuguggca   120
gcauauaauu uaacuuggaa aucaacuaau uucaagacaa uuuuggagug ggaacccaaa   180
cccgucaauc aagucacac uguucaaaua agcacuaagu caggagauug gaaaagcaaa   240
ugcuuuuaca caacagacac agagugugac cucaccgacg agauugugaa ggaugugaag   300
cagacguacu uggcacgggu cuucuccuac ccggcaggga auguggagag caccgguucu   360
gcuggggagc cucuguauga gaaccccca gaguucacac cuuaccugga gacaaaccuc   420
ggacagccaa caauucagag uuuugaacag guggaacaa aagugaaugu gaccguagaa   480
gaugaacgga cuuuagucag aaggaacaac acuuuccuaa gccuccggga uguuuuggc   540 aaggacuuaa uuuauacacu uuauuauugg aaaucuucaa guucaggaaa gaaacagcc   600 aaaacaaaca cuaaugaguu uuugauugau guggauaaag gagaaaacua cuguucagu   660 guucaagcag ugauucccuc ccgaacaguu aaccggaaga uacagacag cccgguagag   720 uguaugggcc aggagaaagg ggaauucaga gaaauauucu acaucauugg agcuguggua   780
uuugugguca ucauccuugu caucauccug gcuauaucuc uacacaagug uagaaaggca   840 ggagugggc agagcuggaa ggagaacucc ccacugaaug uuuca                   885

<210> SEQ ID NO 28
<211> LENGTH: 1876
<212> TYPE: RNA
<213> ORGANISM: mouse

<400> SEQUENCE: 28
ggaggcggcg cggggugggag aggagccggu guccgcgcgg cccuuuauaa cgcaccccgc    60
gccgaccccg gcagccuggg uacagccggu acccaucacu cgcuccccucc gaucgcuccu   120 guagcguagc caacgcgccg ccgcugaagc cccgagaccu cgccccagc ccuuggacau    180 ggcgauccuc gugcgcccgc gccuccuagc ggcucucgcg cccacguuuc ucggcugccu   240
ccuccuccag gugaccgcgg gugcaggcau uccagagaaa gcguuaauu uaacuuggau    300 aucaacugau uucaagacaa uuuuggagug gcaacccaaa cccaccaacu auaccuacac   360
uguacagaua agugaucgau cuagaaacug gaaaaacaag ugcuucucga ccacagacac   420
cgagugcgac cucacagacg agaucgugaa ggaugugacc uggcccuaug aagcaaaggu   480
ccucucuguc ccacggagga acucaguuca uggagacgga gaccaacuug gauucauggu   540
ggaggagccg ccauuuacaa cgcccccaaa guuuuuaccu uaccgagaca caaaccuugg   600
acagccagua auucagcagu uugaacaaga ugguagaaaa cugaacgugg uuguaaaaga   660
cucacuuaca uuagcagaa agaauggguac auuccucacc cugcggcaag cuuuggcaa    720 ggacuugggu uauauaauua cuuaucggaa aggcucaagc acgggaaaga aaacaaacau   780
uacaaacacc aaugaauucu cgauugaugu ggaagaagga guaagcuacu gcuuuuuugu   840
acaagcuaug auuuucucca ggaaaacuaa ccaaaauagc ccaggaagca guacagugug   900
caccgagcaa uggaagaguu ccugggagaa acacucauc auuugggag cagugggugcu   960 ccuggccacc aucuuuauca uccuccuguc cauaucuucug ugcaagcgca gaaagaaccg  1020 agcggggacag aaagggaaga acaccccguc gcgcuuggca uagaggaaag gcugaagccg  1080
cuaacgcuca cacugccugc acggcacugu ugcggagagc ucugauggga acugugcaac  1140
auggagcgug gagccugccg auccuagcuc agagaggcug ccuucauggc cuguuacucc  1200
```

```
agcuaacgcu uugauuccaa cacuagcauu ugucacguua ggacgaacug aaacgguaca    1260
aacugguuaa cacuacagcg ccuuuugcac aaaugcuuua gauuguaugg ucuacacuca    1320
ggaagacacu aggucaccca ggcaaagcca guggacagau gccuuucaua uaaccugggu    1380
gggcuuuugg aaaaucuuug agaaguugau ucauaggcu guagaacagu aaaguggga     1440 cugggcggac uuucuaaca gucguacuuu auaaagcgg uauuggguu uuuuuccu       1500 cgaauaggua cuuuuggaag uucaaagcaa guggcaaacu ucauauaaa cauguaaau    1560 gcaggauauu ucugcuuggg gcaucuuugu gauuuguacu uccuacaau uuagcacuuu    1620 aacugacaau gauggguuu aaacauuuga cagccaacuc uauuuuaua cgacuacuau    1680 acaaagaaac uacauauagu uuuaugauuu aagguacuua gaauguuua ugguuaacau    1740 uguauauauu uacauaaaau uuaaagguuu uguauauggg auuucuauu uauauagcuu    1800 cuauuuguau auuugagau aauuuauuua auauacuuuu auauaaauaa aggugauugg    1860
gaauugagac aaucgc                                                   1876
```

<210> SEQ ID NO 29
<211> LENGTH: 229
<212> TYPE: PRT
<213> ORGANISM: Artificial Sequence
<220> FEATURE:
<223> OTHER INFORMATION: Recombinant hTF

<400> SEQUENCE: 29

```
Met Ser Gly Thr Thr Asn Thr Val Ala Ala Tyr Asn Leu Thr Trp Lys
1               5                   10                  15

Ser Thr Asn Phe Lys Thr Ile Leu Glu Trp Glu Pro Lys Pro Val Asn
            20                  25                  30

Gln Val Tyr Thr Val Gln Ile Ser Thr Lys Ser Gly Asp Trp Lys Ser
        35                  40                  45

Lys Cys Phe Tyr Thr Thr Asp Thr Glu Cys Asp Leu Thr Asp Glu Ile
    50                  55                  60

Val Lys Asp Val Lys Gln Thr Tyr Leu Ala Arg Val Phe Ser Tyr Pro
65                  70                  75                  80

Ala Gly Asn Val Glu Ser Thr Gly Ser Ala Gly Glu Pro Leu Tyr Glu
                85                  90                  95

Asn Ser Pro Glu Phe Thr Pro Tyr Leu Glu Thr Asn Leu Gly Gln Pro
            100                 105                 110

Thr Ile Gln Ser Phe Glu Gln Val Gly Thr Lys Val Asn Val Thr Val
        115                 120                 125

Glu Asp Glu Arg Thr Leu Val Arg Arg Asn Asn Thr Phe Leu Ser Leu
    130                 135                 140

Arg Asp Val Phe Gly Lys Asp Leu Ile Tyr Thr Leu Tyr Tyr Trp Lys
145                 150                 155                 160

Ser Ser Ser Ser Gly Lys Lys Thr Ala Lys Thr Asn Thr Asn Glu Phe
                165                 170                 175

Leu Ile Asp Val Asp Lys Gly Glu Asn Tyr Cys Phe Ser Val Gln Ala
            180                 185                 190

Val Ile Pro Ser Arg Thr Val Asn Arg Lys Ser Thr Asp Ser Pro Val
        195                 200                 205

Glu Cys Met Gly Gln Glu Lys Gly Glu Phe Arg Glu Gly Leu Glu His
    210                 215                 220

His His His His His
225
```

```
<210> SEQ ID NO 30
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 30
nnccatggcc gaggtrmagc ttcaggagtc                                        30

<210> SEQ ID NO 31
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 31
nnccatggcc gaggtbcagc tbcagcagtc                                        30

<210> SEQ ID NO 32
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 32
nnccatggcc gaggtgcagc tgaagsastc                                        30

<210> SEQ ID NO 33
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 33
nnccatggcc gaggtccarc tgcaacartc                                        30

<210> SEQ ID NO 34
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
```

<223> OTHER INFORMATION: n is a, c, g, or t

<400> SEQUENCE: 34
nnccatggcc gaggtycagc tbcagcartc                                    30

<210> SEQ ID NO 35
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 35
nnccatggcc gaggtycarc tgcagcagtc                                    30

<210> SEQ ID NO 36
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 36
nnccatggcc gaggtccacg tgaagcagtc                                    30

<210> SEQ ID NO 37
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 37
nnccatggcc gaggtgaass tggtggaatc                                    30

<210> SEQ ID NO 38
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 38
nnccatggcc gaggtgawgy tggtggagtc                                    30

<210> SEQ ID NO 39
<211> LENGTH: 30
<212> TYPE: DNA
<213> ORGANISM: Artificial Sequence -continued

```
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 39
nnccatggcc gaggtgcags kggtggagtc                                          30

<210> SEQ ID NO 40
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 40
nnccatggcc gaggtgcamc tggtggagtc                                          30

<210> SEQ ID NO 41
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 41
nnccatggcc gaggtgaagc tgatggartc                                          30

<210> SEQ ID NO 42
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 42
nnccatggcc gaggtgcarc ttgttgagtc                                          30

<210> SEQ ID NO 43
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 43
nnccatggcc gaggtraagc ttctcgagtc                                          30
```

```
<210> SEQ ID NO 44
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 44
nnccatggcc gaggtgaars ttgaggagtc                                         30

<210> SEQ ID NO 45
<211> LENGTH: 32
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 45
nnccatggcc gaggttactc traaagwgts tg                                      32

<210> SEQ ID NO 46
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 46
nnccatggcc gaggtccaac tvcagcarcc                                         30

<210> SEQ ID NO 47
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(2)
<223> OTHER INFORMATION: n is a, c, g, or t

<400> SEQUENCE: 47
nnccatggcc gaggtgaact tggaagtgtc                                         30

<210> SEQ ID NO 48
<211> LENGTH: 30
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
```

```
<222> LOCATION: (1)..(2)
<223> OTHER INFORMATION: n is a, c, g, or t

<400> SEQUENCE: 48
nnccatggcc gaggtgaagg tcatcgagtc                                              30

<210> SEQ ID NO 49
<211> LENGTH: 28
<212> TYPE: DNA
<213> ORGANISM: Artificial Sequence
<220> FEATURE:
<223> OTHER INFORMATION: primer for cloning heavy chain of monoclonal
      antibody

<400> SEQUENCE: 49
tgtgcagacc ctcgtggacc acggagca                                                28

<210> SEQ ID NO 50
<211> LENGTH: 28
<212> TYPE: DNA
<213> ORGANISM: Artificial Sequence
<220> FEATURE:
<223> OTHER INFORMATION: primer for cloning heavy chain of monoclonal
      antibody

<400> SEQUENCE: 50
ggactctggg rtcatttacc mggagagt                                                28

<210> SEQ ID NO 51
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 51
nnnngtcgac gctcgayatc cagctgactc agcc                                         34

<210> SEQ ID NO 52
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 52
nnnngtcgac gctcgayatt gttctcwccc agtc                                         34

<210> SEQ ID NO 53
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t
```

```
<400> SEQUENCE: 53
nnnngtcgac gctcgayatt gtgmtmactc agtc                                      34

<210> SEQ ID NO 54
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 54
nnnngtcgac gctcgayatt gtgytracac agtc                                      34

<210> SEQ ID NO 55
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 55
nnnngtcgac gctcgayatt gtratgacmc agtc                                      34

<210> SEQ ID NO 56
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 56
nnnngtcgac gctcgayatt magatramcc agtc                                      34

<210> SEQ ID NO 57
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 57
nnnngtcgac gctcgayatt cagatgaydc agtc                                      34

<210> SEQ ID NO 58
<211> LENGTH: 34
<212> TYPE: DNA
<213> ORGANISM: Artificial Sequence
<220> FEATURE:
```

```
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 58
nnnngtcgac gctcgayaty cagatgacac agac                                    34

<210> SEQ ID NO 59
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 59
nnnngtcgac gctcgayatt gttctcawcc agtc                                    34

<210> SEQ ID NO 60
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 60
nnnngtcgac gctcgayatt gwgctsaccc aatc                                    34

<210> SEQ ID NO 61
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 61
nnnngtcgac gctcgayatt stratgaccc artc                                    34

<210> SEQ ID NO 62
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 62
nnnngtcgac gctcgayrtt ktgatgaccc arac                                    34
```

<210> SEQ ID NO 63
<211> LENGTH: 34
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 63
nnnngtcgac gctcgayatt gtgatgacbc agkc                                34

<210> SEQ ID NO 64
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 64
nnnngtcgac gctcgayatt gtgataacyc agga                                34

<210> SEQ ID NO 65
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 65
nnnngtcgac gctcgayatt gtgatgaccc agwt                                34

<210> SEQ ID NO 66
<211> LENGTH: 34
<212> TYPE: DNA
<213> ORGANISM: Artificial Sequence
<220> FEATURE:
<223> OTHER INFORMATION: primer for cloning light chain of monoclonal
      antibody
<220> FEATURE:
<221> NAME/KEY: misc_feature
<222> LOCATION: (1)..(4)
<223> OTHER INFORMATION: n is a, c, g, or t

<400> SEQUENCE: 66
nnnngtcgac gctcgayatt gtgatgacac aacc                                34

<210> SEQ ID NO 67
<211> LENGTH: 34
<212> TYPE: DNA
<213> ORGANISM: Artificial Sequence
<220> FEATURE:
<223> OTHER INFORMATION: primer for cloning heavy chain of monoclonal
      antibody
<220> FEATURE:
<221> NAME/KEY: misc_feature
<222> LOCATION: (1)..(4)

<223> OTHER INFORMATION: n is a, c, g, or t

<400> SEQUENCE: 67
nnnngtcgac gctcgayatt ttgctgactc agtc                                  34

<210> SEQ ID NO 68
<211> LENGTH: 27
<212> TYPE: DNA
<213> ORGANISM: Artificial Sequence
<220> FEATURE:
<223> OTHER INFORMATION: primer for cloning light chain of monoclonal
      antibody

<400> SEQUENCE: 68
ccttaggagg gaagattgga aggagct                                          27

<210> SEQ ID NO 69
<211> LENGTH: 354
<212> TYPE: DNA
<213> ORGANISM: rat

<400> SEQUENCE: 69
gaggtgcaac tggtggagtc tggtggaggc ttagtacagt ctggaaggtc cctgaagctc       60
tcgtgtgcag cctcaggatt cactttcagt gactataaca tggcctggat ccgccaggct      120
ccaaagaagg gtctggagtg ggtcgcagcc attatttatg atggtactag gacttactat      180
cgagactccg tgaggggccg attcactatc tccagagata tgcaaaaag cacccatatac      240 ctacaagtgg acagtctgag gtctgaggac acggccactt attactgtgc aaccggggat      300
tcctacacca actttgctta ctggggccaa ggcactctgg tcactgtctc ttca            354

<210> SEQ ID NO 70
<211> LENGTH: 318
<212> TYPE: DNA
<213> ORGANISM: rat

<400> SEQUENCE: 70
gagattgtgc tgactcagtc tccaacaacc atggctgcat ctccggggga gaaggtcacc       60
ctcacctgcc gtgccagctc cagtttaagc tacatgcact ggtaccagca gaggtcaggc      120
acctccccca aactctggat ttatgagaca tccaagctgg cttctggagt tccaaatcgc      180
ttcagtggca gtggttctgg gacatctttt tctctcacaa tcgactctat ggagactgag      240
gatgctgcca cttattactg tcagcaggga aatagttacc cacggacgtt cggtggaggc      300
accaagctgg aattgaaa                                                   318

<210> SEQ ID NO 71
<211> LENGTH: 360
<212> TYPE: DNA
<213> ORGANISM: rat

<400> SEQUENCE: 71
gaggtgatgt tggtggagtc aggacctggt ctggtgcagc cctcacagac cctgtccctc       60
atctgcactg tctctggatt ctcattaacg gactacagtg tacactgggt tcgccagcct      120
ccagggaaag gtctggagtg ggtgggagta atgtggagtg gtggaaccac aacatttaat      180
tcaggtctca atcccgact gagcatcagc aggacacct ccaagagcca gtttttctta       240
aaaatgtaca gtctgcgaac tgaagacaca gccgtttact actgtaccag agagagagct      300
gggagccccc tcaattggtt tgcttactgg ggccaaggca ctctggtcac tgtctcttcg      360

<210> SEQ ID NO 72
<211> LENGTH: 321
<212> TYPE: DNA
<213> ORGANISM: rat

<400> SEQUENCE: 72

```
gatattgtga tgacacagtc tcctgcctcc ctgtctgcat ctctggaaga aattgtcacc      60
atcacatgcc aggcaagcca ggacattggt aattacttat catggtatca gcagaaaccg     120
gggaaatctc ctcacctcct gatccatagt tcaaccagct tggcggatgg ggtcccatca     180
aggttcagcg gcagtagatc tggcacacaa tattctctta agatcaacag actccaggtt     240
gaagatactg gagtctatta ctgtcttcag cattatagtg gttctcggac gttcggtggg     300
ggcaccaacc tggaattgaa a                                                321
```

<210> SEQ ID NO 73
<211> LENGTH: 231
<212> TYPE: PRT
<213> ORGANISM: Artificial Sequence
<220> FEATURE:
<223> OTHER INFORMATION: Recombinant mTF

<400> SEQUENCE: 73

```
Met Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
            20                  25                  30

Thr Val Gln Ile Ser Asp Arg Ser Arg Asn Trp Lys Asn Lys Cys Phe
        35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Gln Phe Glu Gln Asp Gly Arg Lys Leu Asn
        115                 120                 125

Val Val Val Lys Asp Ser Leu Thr Leu Val Arg Lys Asn Gly Thr Phe
    130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
            180                 185                 190

Val Gln Ala Met Ile Phe Ser Arg Lys Thr Asn Gln Asn Ser Pro Gly
        195                 200                 205

Ser Ser Thr Val Cys Thr Glu Gln Trp Lys Ser Phe Leu Gly Glu Leu
    210                 215                 220

Glu His His His His His His
225                 230
```

<210> SEQ ID NO 74
<211> LENGTH: 345
<212> TYPE: DNA

<213> ORGANISM: rat

<400> SEQUENCE: 74

| | |
|---|---|
| gaggtgatgt tggtggagtc gggaggaggc ttagtgcagc ctggaaggtc cctgaaactc | 60 |
| tcctgtttag cctctggatt cactttcact gactatggaa tgaactggat tcgtcagact | 120 |
| ccagggaagg gactggaatg ggttgcctct atcactgtta gaaattacat ctactatgca | 180 |
| gacacagtga agggccgatt caccatctcc agggaaaatg ccaagaacac cctgtatttg | 240 |
| cagatgacca gtctgacgtc tgaagacact gccttatatt actgttcaag acgcacggag | 300 |
| ggtatggatt attggggcca aggagtcatg gtcacagtct cctca | 345 |

<210> SEQ ID NO 75
<211> LENGTH: 276
<212> TYPE: DNA
<213> ORGANISM: rat

<400> SEQUENCE: 75

| | |
|---|---|
| gacagagtca ctgtcacctg caaagtgagt cagaatatta tgggtactt aaactggtac | 60 |
| cagcaaaaag ttggagaagc tcccaaagtc ctgatatata atacagacaa tttacaaacg | 120 |
| gacgtaccat cacggttcag tggcagtgga tctgggactt ttttcacact caccatcagc | 180 |
| agcctacacc ctgaagatgt tgccacacat ttctgcttac aacattatag ttggccgctc | 240 |
| acgttcggtt ctgggaccca actggagatc aaacgg | 276 |

<210> SEQ ID NO 76
<211> LENGTH: 1407
<212> TYPE: DNA
<213> ORGANISM: Artificial Sequence
<220> FEATURE:
<223> OTHER INFORMATION: HEAVY CHAIN OF CHIMERIC ANTIBODY NO.1849

<400> SEQUENCE: 76

| | |
|---|---|
| atgtacagga tgcaactcct gtcttgcatt gcactaagtc ttgcacttgt cacgaattcg | 60 |
| gaggtgcaac tggtggagtc tggtggaggc ttagtacagt ctggaaggtc cctgaagctc | 120 |
| tcgtgtgcag cctcaggatt cactttcagt gactataaca tggcctggat ccgccaggct | 180 |
| ccaaagaagg gtctggagtg ggtcgcagcc attatttatg atggtactag gacttactat | 240 |
| cgagactccg tgaggggccg attcactatc tccagagata tgcaaaaag caccctatac | 300 |
| ctacaagtgg acagtctgag gtctgaggac acggccactt attactgtgc aaccggggat | 360 |
| tcctacacca cttttgctta ctggggccaa ggcactctgg tcactgtctc ttcagctagc | 420 |
| accaagggcc catcggtctt ccccctggca ccctcctcca gagcacctc tgggggcaca | 480 |
| gcggccctgg gctgcctggt caaggactac ttccccgaac cggtgacggt gtcgtggaac | 540 |
| tcaggcgccc tgaccagcgg cgtgcacacc ttcccggctg tcctacagtc ctcaggactc | 600 |
| tactccctca gcagcgtggt gaccgtgccc tccagcagct gggcaccca gacctacatc | 660 |
| tgcaacgtga atcacaagcc cagcaacacc aaggtggaca agaaagttga gcccaaatct | 720 |
| tgtgacaaaa ctcacacatg cccaccgtgc ccagcacctg aactcctggg gggaccgtca | 780 |
| gtcttcctct tccccccaaa acccaaggac accctctaca tcacccggga acctgaggtc | 840 |
| acatgcgtgg tggtggacgt gagccacgaa gaccctgagg tcaagttcaa ctggtacgtg | 900 |
| gacggcgtgg aggtgcataa tgccaagaca aagccgcggg aggagcagta caacagcacg | 960 |
| taccgtgtgg tcagcgtcct caccgtcctg caccaggact ggctgaatgg caaggagtac | 1020 |
| aagtgcaagg tctccaacaa agccctccca gcccccatcg agaaaaccat ctccaaagcc | 1080 |

```
aaagggcagc ccgagaacc acaggtgtac accctgcccc catcccggga ggagatgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctga agttccacta cacgcagaag   1380
agcctctccc tgtctccggg taaatga                                      1407
```

<210> SEQ ID NO 77
<211> LENGTH: 702
<212> TYPE: DNA
<213> ORGANISM: Artificial Sequence
<220> FEATURE:
<223> OTHER INFORMATION: LIGHT CHAIN OF CHIMERIC ANTIBODY NO.1849

<400> SEQUENCE: 77

```
atgtacagga tgcaactcct gtcttgcatt gcactaagtc ttgcacttgt cacgaattca    60
gagattgtgc tgactcagtc tccaacaacc atggctgcat ctccggggga aaggtcacc    120 ctcacctgcc gtgccagctc cagtttaagc tacatgcact ggtaccagca gaggtcaggc   180
acctccccca aactctggat ttatgagaca tccaagctgg cttctggagt tccaaatcgc   240
ttcagtggca gtggttctgg gacatctttt tctctcacaa tcgactctat ggagactgag   300
gatgctgcca cttattactg tcagcaggga aatagttacc cacggacgtt cggtggaggc   360
accaagctgg aattgaaacg tacggtggct gcaccatctg tcttcatctt cccgccatct   420
gatgagcagt tgaaatctgg aactgcctct gttgtgtgcc tgctgaataa cttctatccc   480
agagaggcca aagtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt ag                      702
```

<210> SEQ ID NO 78
<211> LENGTH: 468
<212> TYPE: PRT
<213> ORGANISM: Artificial Sequence
<220> FEATURE:
<223> OTHER INFORMATION: HEAVY CHAIN OF CHIMERIC ANTIBODY NO.1849

<400> SEQUENCE: 78

```
Met Tyr Arg Met Gln Leu Leu Ser Cys Ile Ala Leu Ser Leu Ala Leu
1               5                   10                  15

Val Thr Asn Ser Glu Val Gln Leu Val Glu Ser Gly Gly Gly Leu Val
            20                  25                  30

Gln Ser Gly Arg Ser Leu Lys Leu Ser Cys Ala Ala Ser Gly Phe Thr
        35                  40                  45

Phe Ser Asp Tyr Asn Met Ala Trp Ile Arg Gln Ala Pro Lys Lys Gly
    50                  55                  60

Leu Glu Trp Val Ala Ala Ile Ile Tyr Asp Gly Thr Arg Thr Tyr Tyr
65                  70                  75                  80

Arg Asp Ser Val Arg Gly Arg Phe Thr Ile Ser Arg Asp Asn Ala Lys
                85                  90                  95

Ser Thr Leu Tyr Leu Gln Val Asp Ser Leu Arg Ser Glu Asp Thr Ala
            100                 105                 110

Thr Tyr Tyr Cys Ala Thr Gly Asp Ser Tyr Thr Asn Phe Ala Tyr Trp
```

```
            115                 120                 125
Gly Gln Gly Thr Leu Val Thr Val Ser Ser Ala Ser Thr Lys Gly Pro
            130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Tyr Ile Thr Arg Glu Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu Lys Phe His Tyr Thr Gln Lys Ser Leu Ser Leu
        450                 455                 460

Ser Pro Gly Lys
465

<210> SEQ ID NO 79
<211> LENGTH: 233
<212> TYPE: PRT
<213> ORGANISM: Artificial Sequence
<220> FEATURE:
<223> OTHER INFORMATION: LIGHT CHAIN OF CHIMERIC ANTIBODY NO.1849

<400> SEQUENCE: 79

Met Tyr Arg Met Gln Leu Leu Ser Cys Ile Ala Leu Ser Leu Ala Leu
```

```
1               5                   10                  15
Val Thr Asn Ser Glu Ile Val Leu Thr Gln Ser Pro Thr Thr Met Ala
            20                  25                  30

Ala Ser Pro Gly Glu Lys Val Thr Leu Thr Cys Arg Ala Ser Ser Ser
            35                  40                  45

Leu Ser Tyr Met His Trp Tyr Gln Gln Arg Ser Gly Thr Ser Pro Lys
            50                  55                  60

Leu Trp Ile Tyr Glu Thr Ser Lys Leu Ala Ser Gly Val Pro Asn Arg
65                  70                  75                  80

Phe Ser Gly Ser Gly Ser Gly Thr Ser Phe Ser Leu Thr Ile Asp Ser
                85                  90                  95

Met Glu Thr Glu Asp Ala Ala Thr Tyr Tyr Cys Gln Gln Gly Asn Ser
                100                 105                 110

Tyr Pro Arg Thr Phe Gly Gly Gly Thr Lys Leu Glu Leu Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
            210                 215                 220

Thr Lys Ser Phe Asn Arg Gly Glu Cys
225                 230
```